US007914801B1

(12) United States Patent
Holt et al.

(10) Patent No.: US 7,914,801 B1
(45) Date of Patent: Mar. 29, 2011

(54) METABOLIZABLE OIL EMULSION ADJUVANTS AND VACCINES FOR ENHANCING IMMUNO-PROPERTIES OF ANTIBODIES AND THEIR SUBPOPULATIONS

(75) Inventors: Peter S. Holt, Colbert, GA (US); Cam R. Greene, Jefferson, GA (US); Henry D. Stone, Colbert, GA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 407 days.

(21) Appl. No.: 10/887,277

(22) Filed: Jul. 8, 2004

Related U.S. Application Data

(63) Continuation-in-part of application No. 10/101,943, filed on Mar. 21, 2002, now Pat. No. 7,279,163.

(51) Int. Cl.
*A61K 45/00* (2006.01)
*A61K 8/00* (2006.01)
*A61K 8/30* (2006.01)
*A61K 9/00* (2006.01)
*A61K 9/50* (2006.01)

(52) U.S. Cl. ............ 424/278.1; 424/70.19; 424/70.31; 424/400; 424/502

(58) Field of Classification Search ............... 424/70.17, 424/70.31, 184.1, 214.1, 455; 514/937, 938, 514/939, 943
See application file for complete search history.

(56) References Cited

U.S. PATENT DOCUMENTS

| | | | | |
|---|---|---|---|---|
| 4,077,930 A | * | 3/1978 | Lim et al. ................. | 524/801 |
| 4,147,681 A | * | 4/1979 | Lim et al. ................. | 524/813 |
| 5,109,026 A | | 4/1992 | Hoskinson et al. ........... | 514/777 |
| 5,206,316 A | | 4/1993 | Chuang ................. | 252/35 |
| 5,736,125 A | * | 4/1998 | Morawsky et al. ............. | 424/59 |
| 5,744,137 A | * | 4/1998 | Stone ......................... | 424/184.1 |
| 5,817,320 A | | 10/1998 | Stone ......................... | 424/278.1 |
| 5,820,880 A | | 10/1998 | Alving et al. ................. | 424/450 |
| 6,110,492 A | | 8/2000 | Alving et al. ................. | 424/450 |
| 6,235,282 B1 | | 5/2001 | Riviere et al. ............. | 424/184.1 |
| 6,720,001 B2 | | 4/2004 | Chen et al. .................... | 424/455 |

FOREIGN PATENT DOCUMENTS

| | | | |
|---|---|---|---|
| WO | WO 98/44948 | * | 10/1998 |
| WO | WO 9844948 | * | 10/1998 |

OTHER PUBLICATIONS

See Boslego et al (Vaccines and Immunotherapy, 1991, Chapter 17).*
Stone, H., et al., "Influence of Formulation on the Efficacy of Experimental Oil-Emulsion Newcastle Disease Vaccines", *Avian Diseases*, vol. 27(3), pp. 688-697, 1983.
Stone, H., et al., "Preparation of Inactivated Oil-Emulsion Vaccines with Avian Viral or Mycoplasma Antigens", *Avian Diseases*, vol. 22(4), pp. 666-674, 1978.
Stone, H., "Newcastle Disease Oil Emulsion Vaccines Prepared with Animal, Vegetable, and Synthetic Oils", *Avian Diseases*, vol. 41, pp. 591-597, 1997.
Stone, H., "Efficacy of Experimental Animal and Vegetable Oil-Emulsion Vaccines for Newcastle Disease and Avian Influenza", *Avian Diseases*, vol. 37, pp. 399-405, 1993.

* cited by examiner

*Primary Examiner* — Vanessa L. Ford
(74) *Attorney, Agent, or Firm* — John Fado; Albert Y. Tsui; Lesley Shaw

(57) ABSTRACT

Water-in-oil priming emulsion vaccines increase the titers and/or avidity indexes of antibodies following a second dose of a commercial or experimental vaccine resulting in increased protection for disease in animal.

5 Claims, 32 Drawing Sheets
(1 of 32 Drawing Sheet(s) Filed in Color)

NDV Hexadecane Vaccine Serum HI titers

Fig. 10b

METABOLIZABLE OIL EMULSION ADJUVANTS AND VACCINES FOR ENHANCING IMMUNO-PROPERTIES OF ANTIBODIES AND THEIR SUBPOPULATIONS

This is a Continuation-In-Part application of patent application Ser. No. 10/101,943, filed Mar. 21, 2002, still pending and herein incorporated by reference in its entirety.

BACKGROUND OF THE INVENTION

1. Field of the Invention

This invention relates to the control of disease in animals through the use of oil emulsion adjuvants per se and emulsion priming vaccines containing fatty acid esters, emulsifiers, and surfactants.

2. Description of the Related Art

Vaccines are used for the prevention of disease in animals. The cornerstone of many infectious disease control programs is the induction of specific immunity by vaccination with either live or inactivated microorganisms or their products. Vaccine efficacy depends on many variables, such as the nature and the amount of antigen administered and the presence of adjuvants to enhance immunogenicity. Further, the presence of specific antibody in the serum of young animals, passively acquired from the mother, can seriously impact the effectiveness of the immunization regime.

Water-in-oil vaccines have proven to be more efficacious than vaccines comprised of oil-in-water or aqueous antigen or oil phase alone (Stone, Avian Dis., Volume 27(3), 688-697, 1993). Stone et al. (Av Dis., Volume 34, 979-983, 1990) disclose the use of the terpene oils, squalene and squalane, in a vaccine for Newcastle disease in place of mineral oil. They found that the cumulative HI titers using these oils were similar to mineral oil but the viscosity was up to four times greater than those vaccines using mineral oil. The supply for these terpene oils is limited and more expensive.

Stone (1993, supra) discloses water-in-oil vaccines using animal and vegetable oils. The vaccines contained an aqueous antigen with an oil phase-to-aqueous phase ratio of 4:1. Emulsification was done with both oil-soluble and water-soluble surfactant added to the oil phase. Beeswax was used as an emulsifier for the non-mineral oil vaccines since the known mineral oil surfactants were not suitable for animal and vegetable oil-containing emulsion vaccines. It was reported that the non-mineral oil containing emulsion vaccines had a higher viscosity than mineral oil emulsions of the same relative oil and aqueous components. Low viscosity is an important characteristic for oil emulsion vaccines because it eases the vaccination process, lowering fatigue of working, saving time and work when large numbers of birds are involved. Low viscosity of the oil phase also allows emulsification of a greater amount of aqueous phase for increased volume of antigen or multiple antigens before prohibitive viscosity is reached.

U.S. Pat. No. 5,109,026 to Hoskinson et al., discloses water-in-oil vaccines with mineral oils, squalene, and squalane. The water phase includes a polyanionic polyelectrolyte. Emulsifiers such as ARLACEL A (mannide monooleate) and ARLACEL 80 (sorbitan oleate) were added as oil-soluble emulsifiers with TWEEN 80 (polysorbate 80) as water-soluable emulsifier.

The accepted emulsifying agents for mineral oil vaccines are ARLACEL A (mannide monooleate), ARLACEL 80 (sorbitan oleate), and 80 (polysorbate 80). These easily emulsify water phases in mineral oil but do not function in the same capacity with non-mineral oils. Beeswax is suggested as a surface-active agent for use with non-mineral oil vaccines. However, the beeswax-containing emulsion vaccines have viscosities that are much higher than mineral oil vaccines using emulsifying agents such as ARLACEL A (mannide monooleate) or ARLACEL 80 (polysorbate 80 and TWEEN 80 (polysorbate 80) (Stone, Avian Diseases, Volume 37, 399-405, 1993).

While various water-in-oil vaccines have been developed, there remains a need in the art for oil emulsion formulations to enhance immune responses. The present invention provides oil-emulsion priming vaccines and their non-antigen counterparts. These formulations are different from prior art compositions and their application improves secondary immune responses through increased specific antibody titers and/or avidity and non-specific innate immunity.

SUMMARY OF THE INVENTION

It is therefore an object of the present invention to provide a priming water-in-oil emulsion vaccine that contains a fatty acid ester, an emulsifier, and a mixture of at least two surfactants.

A further object of the present invention is to provide a priming water-in-oil emulsion composition having a $C_{18}$ to $C_{32}$ fatty acid ester, an emulsifier, and a mixture of at least two surfactants.

A still further object of the present invention is to provide a priming water-in-oil emulsion vaccine having a $C_{18}$-$C_{32}$ fatty acid ester, isostearyl diglycerol succinate (IMWITOR 780K, Sasol, South Africa), a mixture of polyoxyethylene sorbitan trioleate and sorbitan trioleate.

Another object of the present invention is to provide a method that includes injecting an animal with a vaccine including a priming emulsion wherein said vaccine includes a $C_{18}$-$C_{32}$ fatty acid ester, Isostearyl diglycerol succinate, a mixture of polyoxyethylene sorbitan trioleate and sorbitan trioleate.

A still further object of the present invention is to provide methods that include priming avian embryos for post-hatch vaccination by injecting a priming water-in-oil emulsion with or without antigen containing a $C_{18}$-$C_{32}$ fatty acid ester, an emulsifier, and a mixture of at least two surfactants.

Further objects and advantages of the invention will become apparent from the following description.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 8A compares the % intestinal *Salmonella enteriditis* present at 13 days and 19 days post challenge. FIG. 8B is a comparison of the number of *Salmonella enteriditis* per gram of cecum 13 days and 19 days post challenge. FIG. 8C is a comparison of vaccines for % liver *Salmonella enteriditis* 13 and 19 days post challenge and FIG. 8D is a comparison of number of *Salmonella enteriditis* per gram of liver tissue at 13 and 19 days post challenge.

FIG. 9A compares the % intestinal *Salmonella enteriditis* present at 7 days and 15 days post challenge. FIG. 9B is a comparison of the number of *Salmonella enteriditis* per gram of cecum 7 days and 15 days post challenge. FIG. 9C is a comparison of the vaccines for % liver *Salmonella enteriditis* 7 and 15 days post challenge and FIG. 9D is a comparison of the number of *Salmonella enteriditis* per gram of liver tissue at 7 and 15 days post challenge.

FIG. 10b is a graph showing serum HI-titer in hens receiving NewCastle Disease Virus n-hexadecane vaccine.

DETAILED DESCRIPTION OF THE INVENTION

Figure 1:
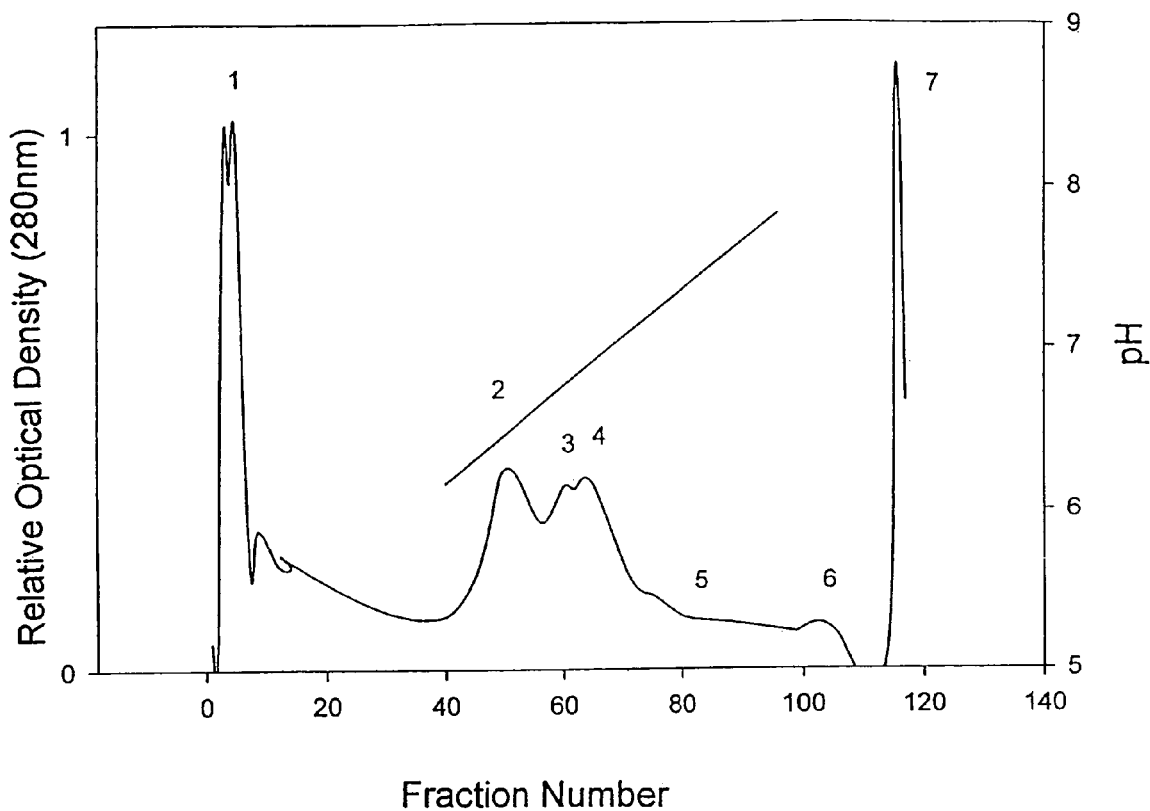
FIG. 1 is a graph of an IminoDiacetic Acid Iron sepharose B column (IDA-$Fe^{3+}$) chromatograph of non-immunized chicken serum.

The vaccine formulations of the present invention are applicable to any animal and are especially useful in avian species, whether domestic or wild, and particularly to those which are commercially reared for meat or egg production. Without limitation thereto, exemplary avians include chickens, turkeys, geese, ducks, pheasant, emu, ostrich, etc.

One advantage of the present invention is in the prevention of lethal diseases such as those which threaten avians. Avian diseases include any disease or contamination of viral, bacterial, or other microbial origin. Examples of such, without limitation thereto, include Salmonella, Newcastle disease, avian leukosis, infectious bursal disease, adenovirus disease, reovirus, pox, laryngotracheitis, avian influenza, Marek's disease, etc. The present invention water-in-oil emulsion vaccines induce higher biliary IgA (Table 1) responses which decreases mucosal/internal organ invasion and fecal shedding, increase specific activity of serum IgG subpopulations, and increase the relative avidity index of serum IgG subpopulations, causing increased protection. The vaccines of the present invention provide excellent protection against organ invasion and significantly reduce intestinal enteropathogenic bacteria levels when compared to two of the three commercial preparations during challenge studies. Furthermore, the vaccines of the present invention are useful for in ovo vaccination to stimulate early immune protection. The present invention includes water-in-oil emulsion priming vaccines which increase the titers and/or avidity indexes, i.e. strength of antigen binding of antibodies following a second dose of commercial or experimental vaccine. Previous studies have shown that high avidity antibodies correlate with increased protection. The priming vaccine works with or without antigen and is effective for a broad range of chicken ages including embryo vaccination. A priming dose without antigen stimulates nonspecific (innate) immunity. The priming emulsion vaccine is useful for in ovo vaccination to stimulate early immune response. A non-antigen priming emulsion is especially important in those instances when passively acquired maternal antibody would interfere with a specific antigen-driven response. In combination, the fatty acid ester priming emulsion vaccines and the water-in-oil emulsion vaccines give a secondary boost to increase IgG activity. The present invention is also useful for the production of monoclonal antibodies, adaptable to water-in-oil-in-water emulsions and an approach to circumvent the detrimental effects of maternal immunity.

The term vaccine is defined to mean all types of biological agents used to produce active immunity or competitive exclusion. More particular, the present invention is drawn to water-in-oil vaccine formulations.

Examples of oils useful for the secondary dose in the present invention include $C_{14}$ to $C_{18}$ aliphatic straight-chain saturated hydrocarbons, such as for example, hexadecane, isohexadecane, pentadecane, heptadecane, octadecane, tetradecane, etc.

The emulsifier used in the present invention is a hydrophobic nonionic surfactant, isostearyl diglycerol succinate (IMWITOR 780K). The co-surfactants of the present invention are polyoxyethylene sorbitan trioleate and sorbitan trioleate.

Examples of $C_{18}$ to $C_{32}$ fatty acid esters useful in the present invention include butyl stearate, butyl myristate, trideceyl stearate, octastearate, isopropyl myristate, isocetyl myristate, isopropyl isostearate, etc. and mixtures thereof.

The water-in-oil vaccines and priming vaccines are prepared using an oil to aqueous phase (O:A) of approximately 4 parts oil to approximately 1 part aqueous phase (volume: volume). The surfactant mixture is added to the oil phase or to the aqueous phase for approximately 2-3 minutes on a rotor Stator model Pro400 (ProScientific, Inc., Monroe, Conn.) at a maximum speed of about 7500 rpm. The aqueous phase consists of antigen prepared in PBS or normal allantoic fluid. The antigen can be live or inactivated. The aqueous phase with or without antigen is added to the oil phase which contains the surfactant under continual homogenization. For large volumes of water-in-oil emulsion vaccines, the aqueous antigen is usually added to the oil phase and dispersed during stir. Mineral oil vaccines are prepared as described by Stone et al., Avian Diseases, Volume 22, 666-674, 1978; and Stone et al., Avian Diseases, Volume 34, 979-983, 1990; which are both herein incorporated by reference. Total surfactant volume for vaccines is approximately 20% of the oil phase.

The priming vaccines are prepared by mixing about 1 part isostearyl diglycerol succinate (IMWITOR 780K), about 0.7 parts polyoxyethylene sorbitan trioleate (TWEEN-85), and about 0.3 parts sorbitan trioleate (SPAN-85) and about 8 parts of fatty acid ester to form an oil phase. About 8 parts of the oil phase is mixed with about 2 parts of an aqueous phase with or without antigen. The aqueous phase is any aqueous substance known to be used in vaccine preparation such as, for example, phosphate buffered saline (PBS), allantoic fluid, etc. The oil and aqueous phases are mixed as described above.

For industrial preparation of the surfactant composition-containing water-in-oil emulsion vaccines, the oil and surfactant-containing aqueous phases are mixed with a Silverson turbine by mixing for about 5 minutes at about 30° C.

The following examples are intended only to further illustrate the invention and are not intended to limit the scope of the invention which is defined by the claims. An inactivated *Salmonella enterica* serovar. *enteriditis* (SE) is used as a model system for the present invention.

Example 1

Three (3) specific-pathogen free White Leghorn hen birds (3 birds/emulsion/experiment) were immunized subcutaneously, in the neck region, with a water-in-oil (w/o) emulsion containing inactivated Salmonella enterica serovar enteriditis (SE). Each bird received about a 100 µg dose of avetone-inactivated SE serovar enteriditis whole cells contained within about a 500 µl injection volume. Serum samples, collected by venous wing vein puncture, were obtained at about three (3) weeks post-primary immunization and were stored at about −20° C. until used. The oils tested included Marcol-52 (Mineral Oil, Esso Chemicals, Toronto, Canada) and n-hexadecane (Sigma Chemical Co., St. Louis, Mo.). To test emulsion composition, MARCOL-52 and n-hexadecane were formulated in the following manner: about 8 m; pf n-hexadecane or MARCOL-52, about 1 ml sorbitan monooleate (ARLACEL 80; ICI United States, Wilmington, Del.), about 0.7 ml polyoxyethylene sorbitan trioleate (TWEEN 85; Fisher Scientific Company), about 0.3 ml sorbitan trioleate (SPAN 85; Sigma Scientific Company) to form formulation 1. The antigen is about 5 mg/ml in distilled water. Approximately 8 ml of formulation 1 is mixed with about 2 ml of antigen. The antigen is drawn up into a 3 ml syringe having a 25 g needle. It is slowly added to formulation 1 while mixing at about 7500 rpms. Mixing continues until all of the antigen has been added. A second formulation includes about 8 ml n-hexadecane or MARCOL-52, about 1 ml sorbitan monooleate (ARLACEL 80), about 0.75 ml polyoxyethylene sorbitan monooleate (TWEEN 80, Polysorbate 80; Fisher Scientific, Atlanta, Ga.), about 0.3 ml sorbitan monooleate (80; Sigma Chemical Company) to form formulation 2. This is mixed with the antigen as described above.

The serum samples collected from the immunized chickens were applied to an Iron Chelate Chromatography column in order to separate the IgG into subpopulations. Iminodiacetic acid (IDA) epoxy-activated Sepharose 6B (Pharmacia Biotech, Piscataway, N.J.) was poured into a G10×150 Moduline medium pressure laboratory column (Amicon, Beverly, Mass.) to obtain a final packing bed volume of about 7.5 ml. Following equilibration with deionized water, the column was converted to the IDA-$Fe^{3+}$ form by charging with aqueous $FeCl_3.6H_2O$. After charging, the column was washed with deionized water and then equilibrated with about 50 mM MES (2-[N-Morpholino]ethanesulfonic acid) about pH 6 (Sulkowski, Makromol. Chem. Macromol. Symp., Volume 17, 335, 1988). After completion of each run, the IDA gel is stripped (chelate annihilation) with about 50 mM EDTA+ about 500 mM NaCl about pH 7 and regenerated.

About a 350 µl delipidzed serum sample is applied to the column after buffer removal from the top of the column bed. The serum sample was allowed to enter the column bed at a flow rate of about 1 ml/min while the fraction collector was operated in the time collection mode at about 3 min/tube and a sensitivity setting of about 0.1 AUFS. The column was subsequently refilled with buffer. The column was washed with the equilibration buffer until the unabsorbed peak returned to baseline. Bound proteins and immunoglobulins were eluted using an ascending linear pH gradient of about pH 6 to about pH 8 consisting of about 100 ml equilibration buffer and about 100 ml of about 50 mM HEPES (N[2- hydroxyethyl]piperazine-N'-[2-ethane-sulfonic acid]), about pH 8 (Sulkowski, 1988; supra). Following gradient completion, the column was washed with about 50 mM HEPES, about pH 8, and subjected to the late annihilation. Each protein-containing peak was tested for the presence of IgG using the Ouchterlony double diffusion technique and for immunological activity using the enzyme-linked immunosorbent assay (ELISA), while the total IgG content for each peak was determined using the single radial immunodiffusion method (Fahey and McKelvey, Quantitative Determination of Serum Immunoglobulins in Antibody-Agar Plates, J. Immunol., Volume 94, 84-90, 1965).

For the ELISA, purified SE flagella (Ibrahim et al., J. Clin. Micro., Volume 22, 1040, 1985), diluted to about 1 µg/ml in about 100 mM bicarbonate buffer about pH 9.6, was bound to the solid phase by incubation for about two hours at about 37° C. followed by overnight incubation at about 4° C. Following immobilization, the microtiter plate (solid phase) (Immulon 4, Dynatech Laboratories, Chantilly, Va.) was blocked with about 100 mM phosphate buffer (PB)+about 1% (W/V) polyvinylpyrrolidone, about pH 8, for about 1 hour at about 37° C. After blocking, the microtiter plate was washed twice with about 20 mM PBS+about 0.05% (V/V) Tween-20, about pH 7.4 (PBST), and then two-fold dilutions, diluted in PBST, of each eluted subpopulation were added to the appropriate wells of the microtiter plate and incubated overnight at about 4° C. The plate was washed twice with PBST and alkaline phosphatase labeled affinity purified rabbit anti-chicken IgG Heavy and Light chain antiserum (Jackson ImmunoResearch Laboratories, West Grove Pa.), diluted about 1:5000 in PBST, was added to the plate and incubated for about 60 minutes at about 37° C. After twice washing the plate with PBST, p-nitrophenyl phosphate, about 1 mg/ml diethanolamine buffer at about pH 9.8, was added to the appropriate wells of the microtiter plate. Color development was allowed to proceed for about 30 minutes at about room temperature and was stopped by the addition of about 3N NaOH. Absorbance was measured at about $405_{nm}$ using a Multiscan MS microtiter plate reader (Labsystems, Needham, Mass.).

The relative avidity index (RAI) for each subpopulation of IgG was determined using about 6M and 8M Urea as previously described by Chargelegue et al. (Clin. Exp. Immunol., Volume 93, 331, 1993). Statistical differences for the relative avidity index were determined by Students' t-test or the Rank Sum Test using SigmaStat software version 1.0 (Jandel Scientific Corn., San Rafael, Calif.).

Immunoelectrophoresis (IEP) was performed in about 1% (w/v) agarose (Type Medium EEO, Sigma Chemical Co.) in Tris-Tricine buffer, about pH 8.6. Samples of 5 µl each were electrophoresed in an EC 360 flatbed apparatus (E-C Apparatus Corp., St. Petersburg, Fla.) at about 200 constant volts for about 45 minutes. After electrophoresis, the IEP films were incubated overnight in a humidity box and then processed and stained with about 0.1% (w/v) coomassie brilliant blue R-250 (Sigma Chemical Co.).

Normal chicken serum (non-immune serum) from non-immunized birds, was chromatographed on a previously equilibrated IDA-$Fe^{3+}$ column (FIG. 1). Using an ascending linear pH gradient, seven IgG containing peaks, as confirmed by double diffusion analysis, were resolved. Peak 1 comprises the unabsorbed fraction, while peaks 2-5 elute during gradient formation. Peak 6 is eluted during the about pH 8 washing step, while peak 7 is collected during the chelate annihilation phase. Analysis of the elution pH indicates that peak 2 elutes from approximately pH 6.15-6.52; peak 3 from approximately pH 6.57-6.90; peak 4 from approximately pH 6.90-7.53; while peak 5 elutes from approximately 7.53-7.75.

Figure 2:
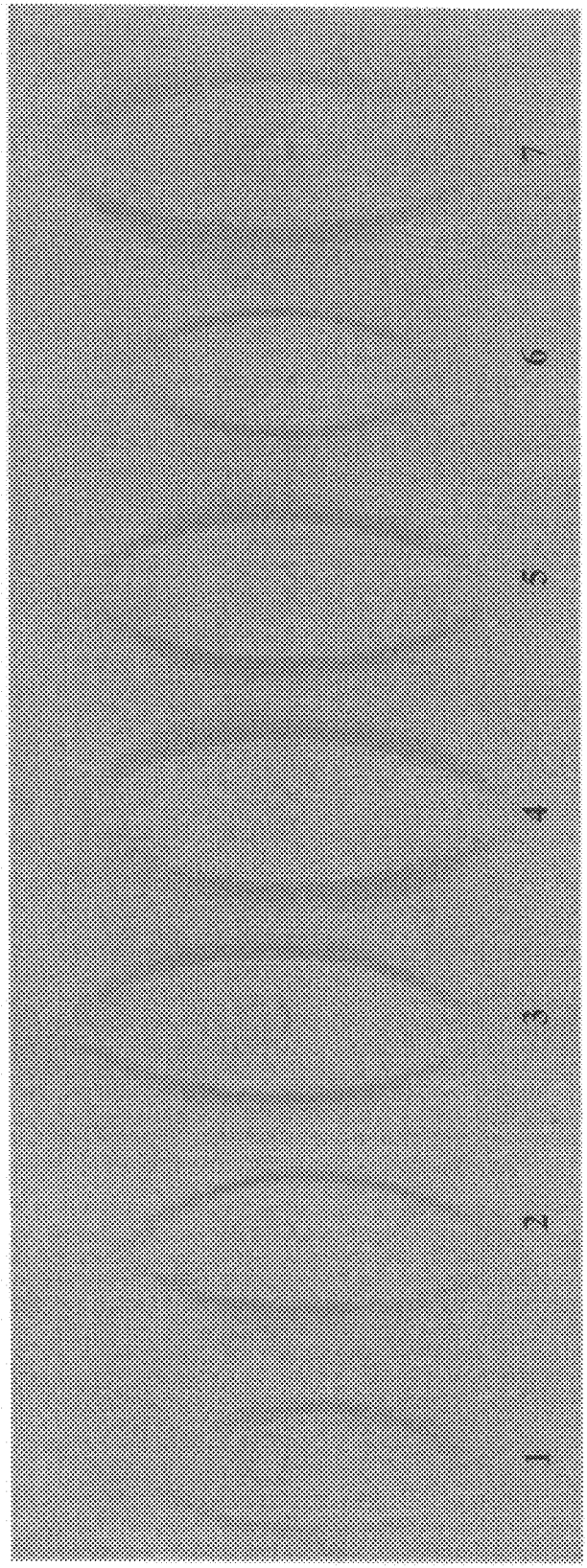
FIG. 2 is a photograph showing the immunoelectrophoresis (IEP) of IgG subpopulations of non-immune serum from hens.

Examination of each IgG subpopulation by immunoelectrophoresis demonstrates an electrophoretic mobility difference (FIG. 2). This difference is clearly demonstrated between peaks 1 and 7, while minor differences exist between peaks 2-6.

Figure 3A:
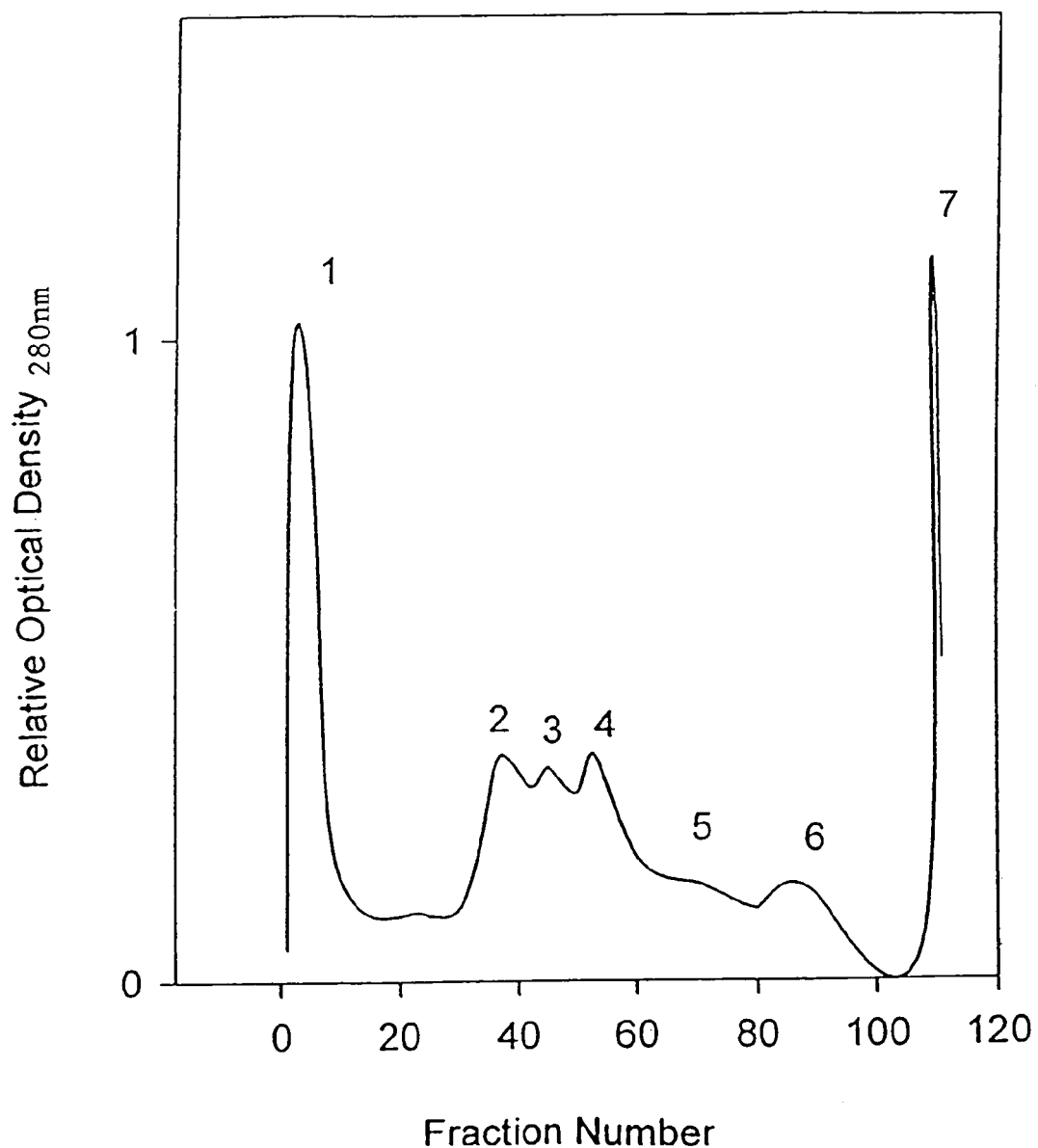
FIGS. 3A-3C are graphs showing (3A) IDA-$Fe^{3+}$ chromatography of serum from hens receiving a MARCOL 52 (mineral oil) emulsion containing polyoxyethylene sorbitan monooleate and sorbitan monooleate; (3B) ELISA endpoint for serum from hens receiving MARCOL 52/polyoxyethylene sorbitan monooleate/sorbitan monooleate; (3C) Relative avidity Index for serum IgG subpopulations from hens receiving MARCOL 52/polyoxyethylene sorbitan monooleate/sorbitan monooleate.
Figure 3B:
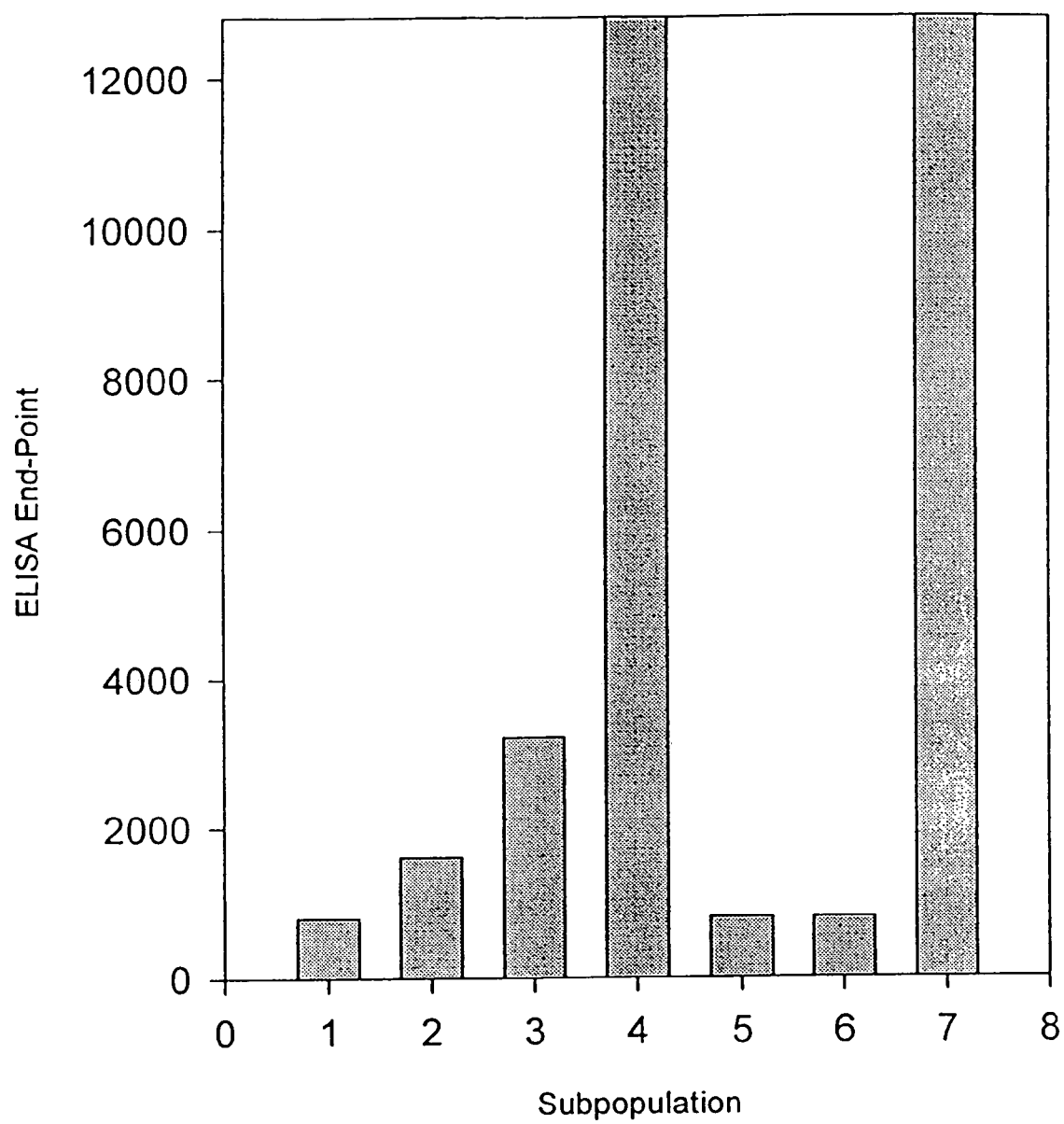
Figure 3C:
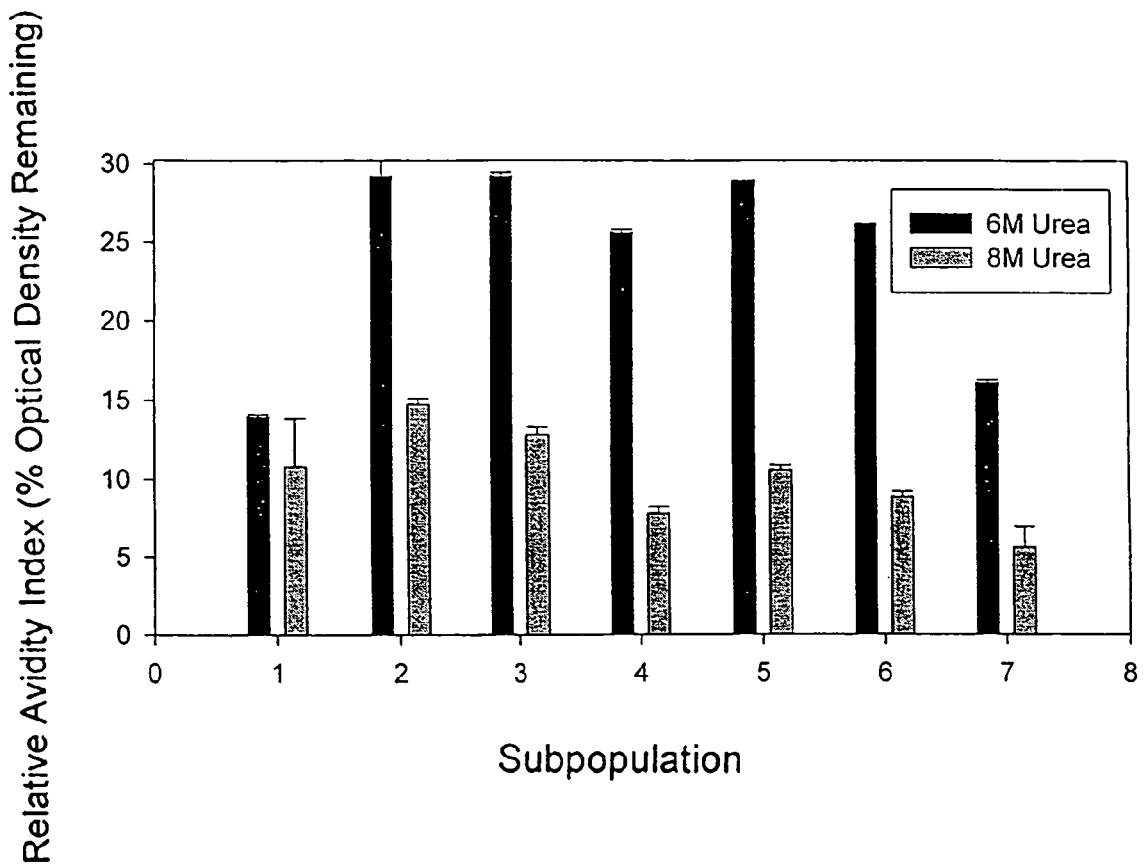

Serum from hens immunized the mineral oil water-in-oil emulsion vaccine containing mineral oil (MARCOL-52), sorbitan monooleate (ARLACEL-80), polyoxyethylene sorbitan monooleate (TWEEN-80) and sorbitan monooleate (SPAN-80) shows a profile very similar to normal chicken serum but with some notable exceptions: peaks 3 and 4 are more resolved, while peak 4 is enhanced, and the almost complete absence of peak 5 (FIG. 3A). Immunological activity (tested by ELISA) was detected in all peaks with peaks 4 and 7 exhibiting the highest activity (FIG. 3B). The relative avidity index was determined for each IgG subpopulation. This emulsion primarily elicits low avidity antibodies and the distribution of high avidity antibodies is skewered towards subpopulations that do not bind to the column or else elute very early in the gradient formation; that is, the relative percentages of high activity antibodies decrease with increasing net positive charge (FIG. 3C).

Figure 4A:
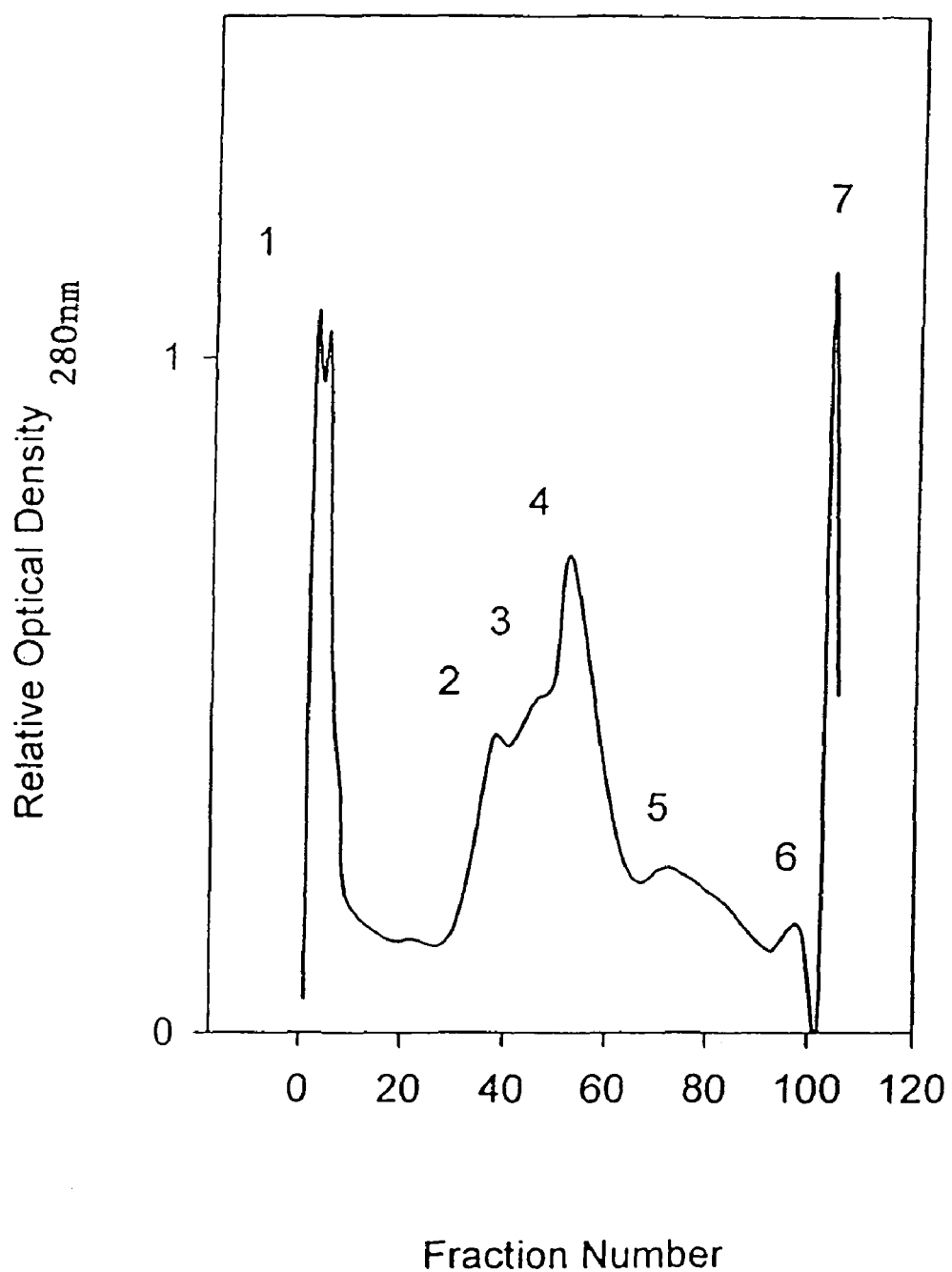
FIGS. 4A-4D are graphs showing: (4A) IDA-$Fe^{3+}$ chromatography of serum from hens receiving MARCOL 52 emulsion containing polyoxyethylene sorbitan trioleate and sorbitan trioleate; (4B) ELISA end-point comparisons for serum from hens receiving MARCOL 52 emulsion containing polyoxyethylene sorbitan trioleate and sorbitan trioleate; (4C) Comparison of Relative Avidity Indexes (6M Urea) for serum from hens receiving MARCOL 52 emulsion containing polyoxyethylene sorbitan monooleate and sorbitan monooleate vs. polyoxyethylene sorbitan trioleate/sorbitan trioleate.
Figure 4B:
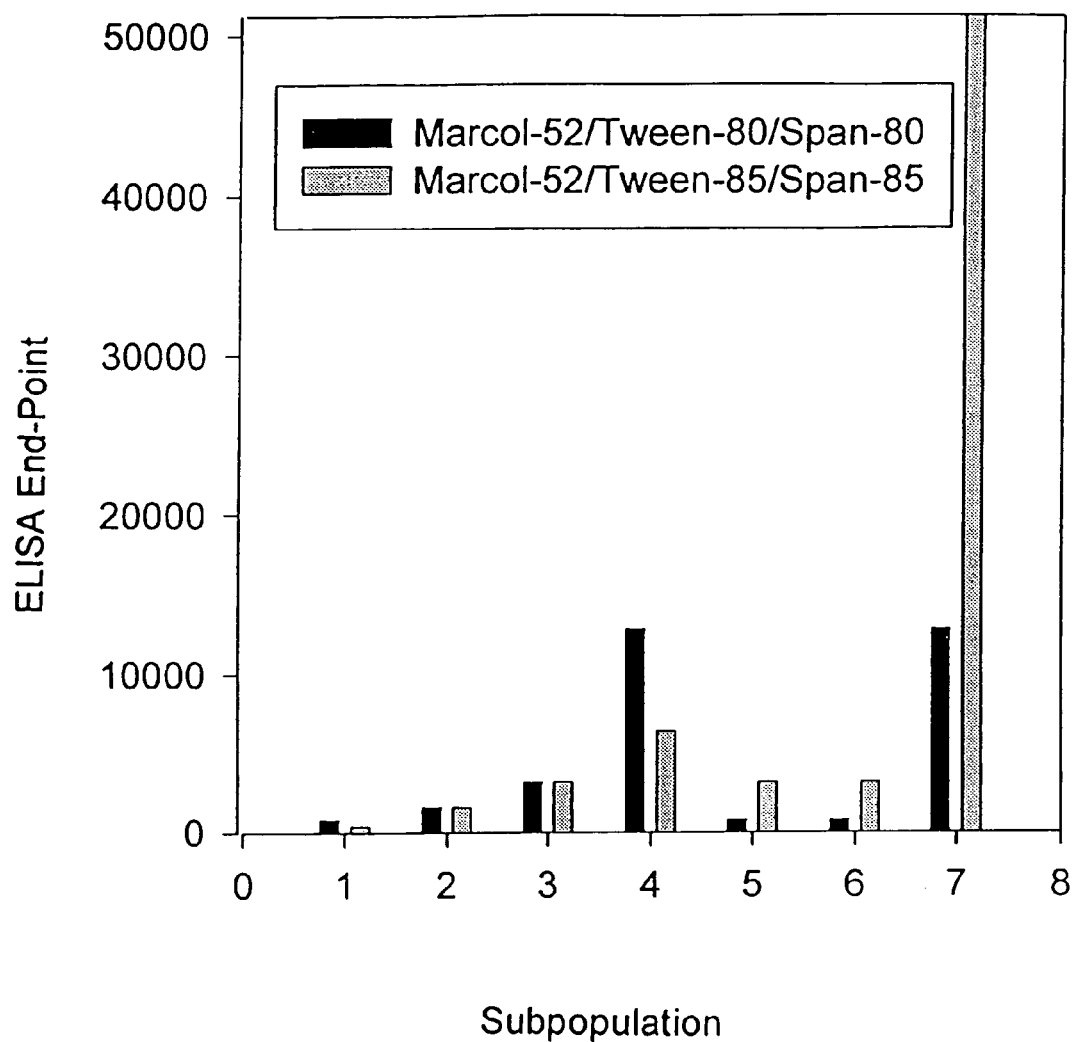
Figure 4C:
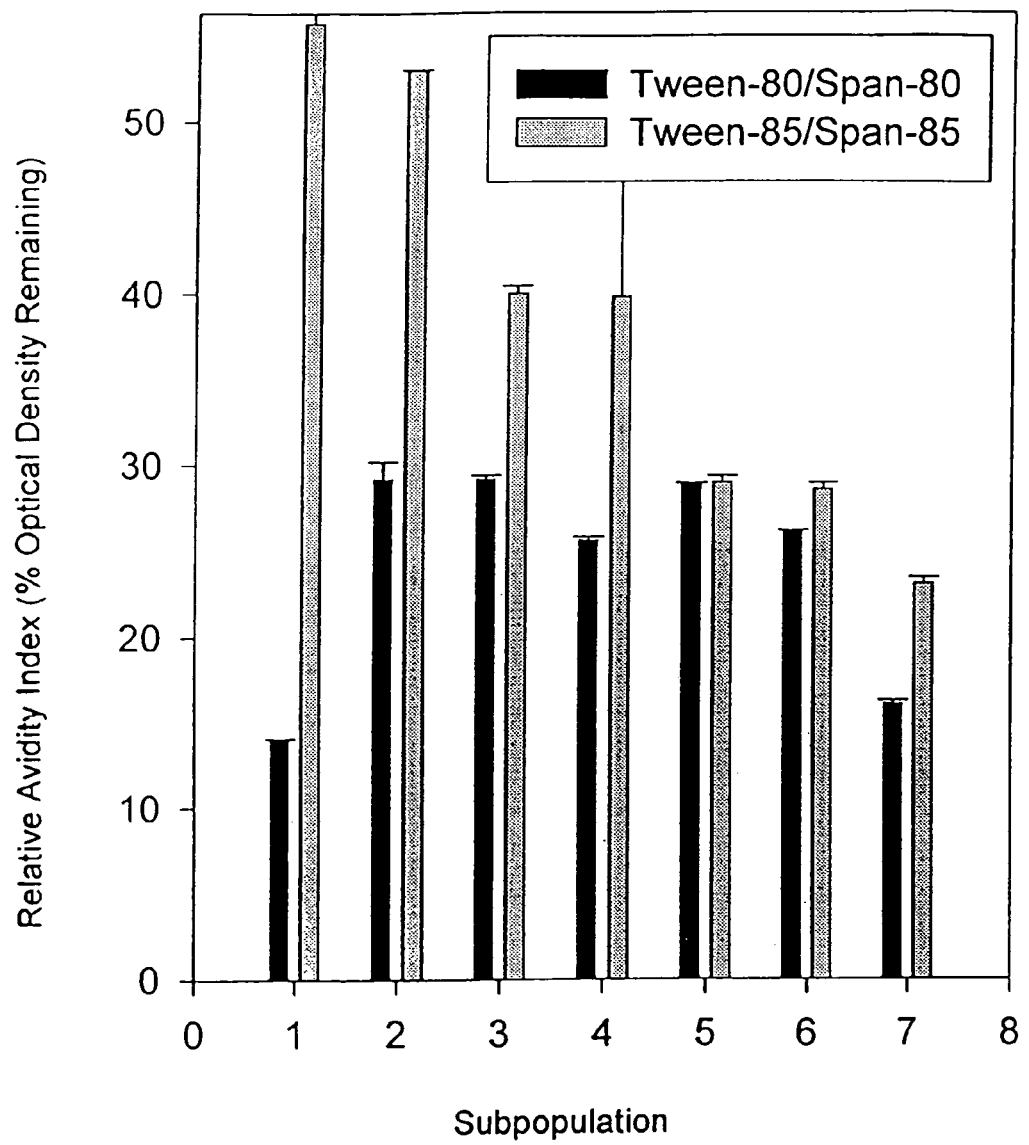
Figure 4D:
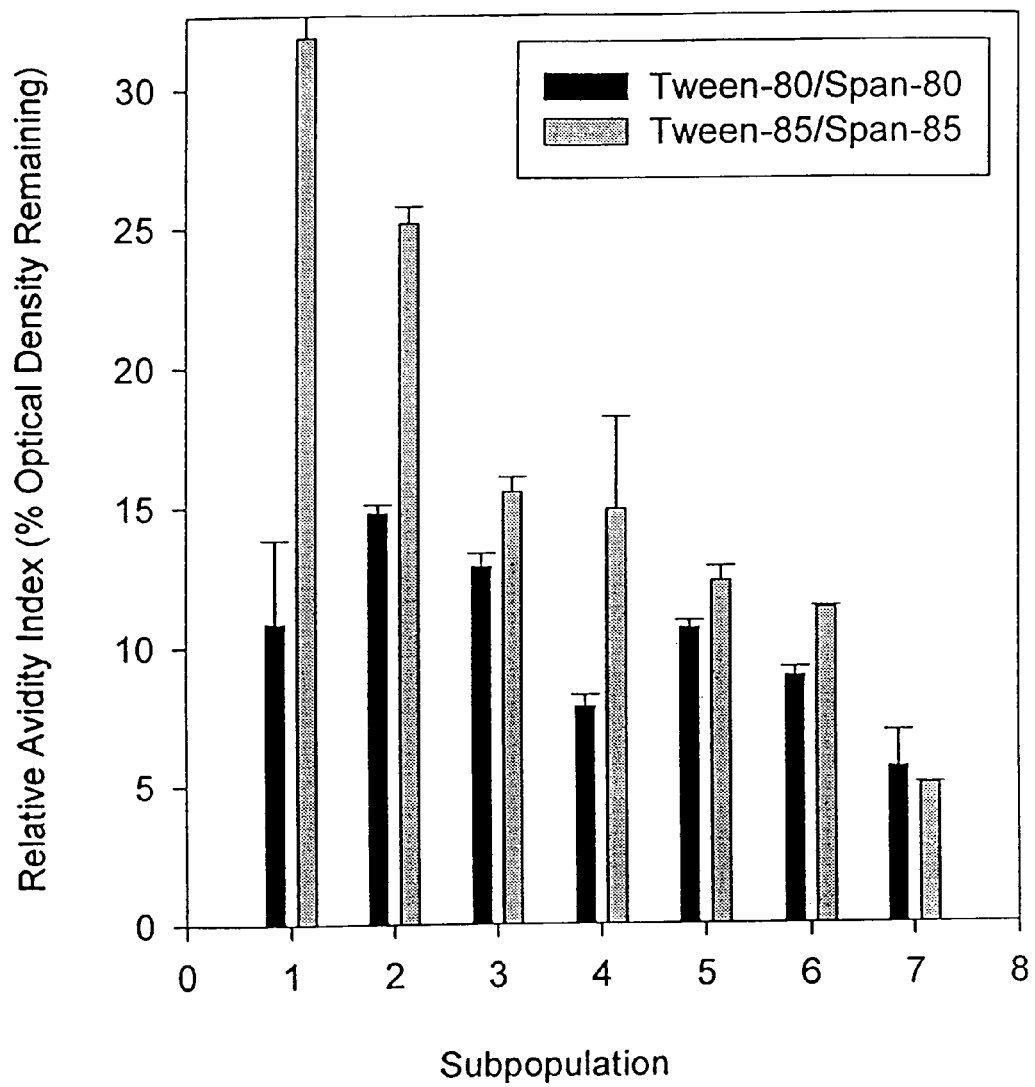

The mineral oil (MARCOL-52), sorbitan monooleate (ARLACEL-80), polyoxyethylene sorbitan trioleate (TWEEN 85), and sorbitan trioleate (SPAN 85) emulsion vaccine was used to test the effect of the emulsion composition. The serum chromatography profile for this emulsion is quite different from that previously seen: peaks 2-6 have been greatly enhanced (FIG. 4A), while the immunological activity for peaks 5 and 6, and especially 7 have been highly upregulated (FIG. 4S). By substituting polyoxyethylene sorbitan monooleate (TWEEN 80) and sorbitan monooleate (SPAN 80) with polyoxyethylene sorbitan trioleate (TWEEN 85) and sorbitan trioleate (SPAN 85), the relative avidity index for both high and low avidity antibodies have been upregulated for subpopulations 1-4 and is statistically significant (6M, P=0.0029; 8M, P=0.0326) (FIGS. 4C and 4D).

Figure 5A:
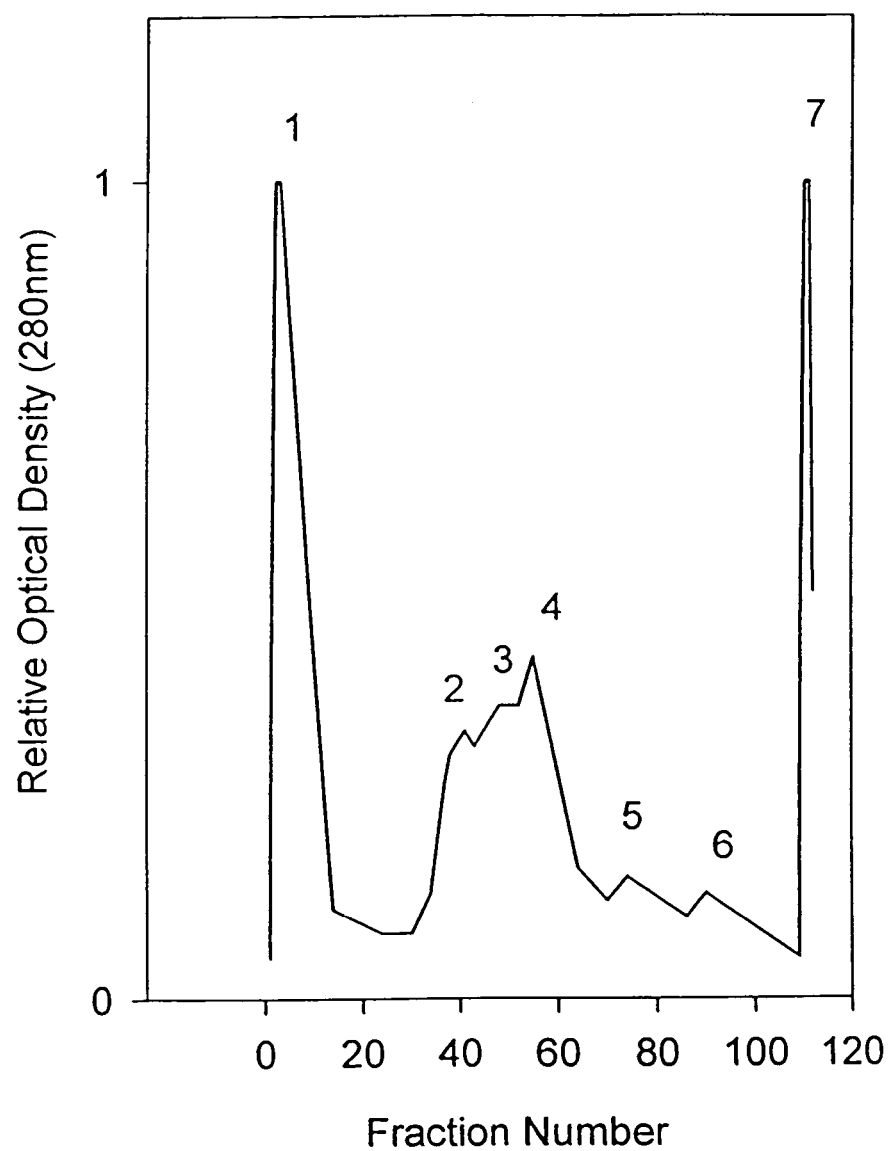
FIGS. 5A-5C are graphs showing: (5A) IDA-$Fe^{3+}$ chromatography of immune serum taken three weeks post-vaccination from hens receiving n-hexadecane emulsion containing polyoxyethylene sorbitan monooleate and sorbitan monooleate; (5B) ELISA end-point for serum from hens receiving n-hexadecane emulsion containing polyoxyethylene sorbitan monooleate and sorbitan monooleate; and (5C) Relative Avidity Index for serum from hens receiving n-hexadecane emulsion containing polyoxyethylene sorbitan monooleate and sorbitan monooleate.
Figure 5B:
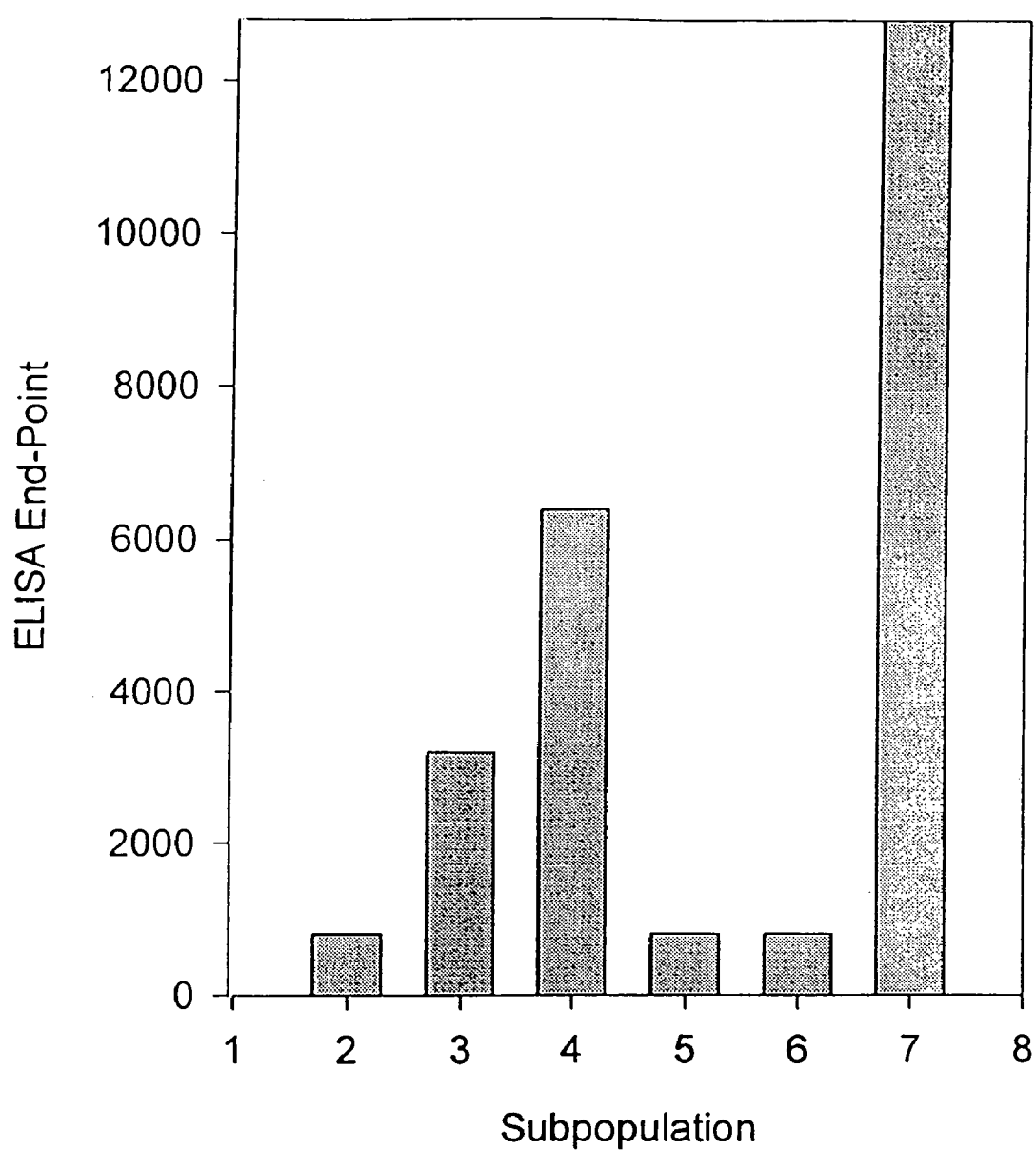
Figure 5C:
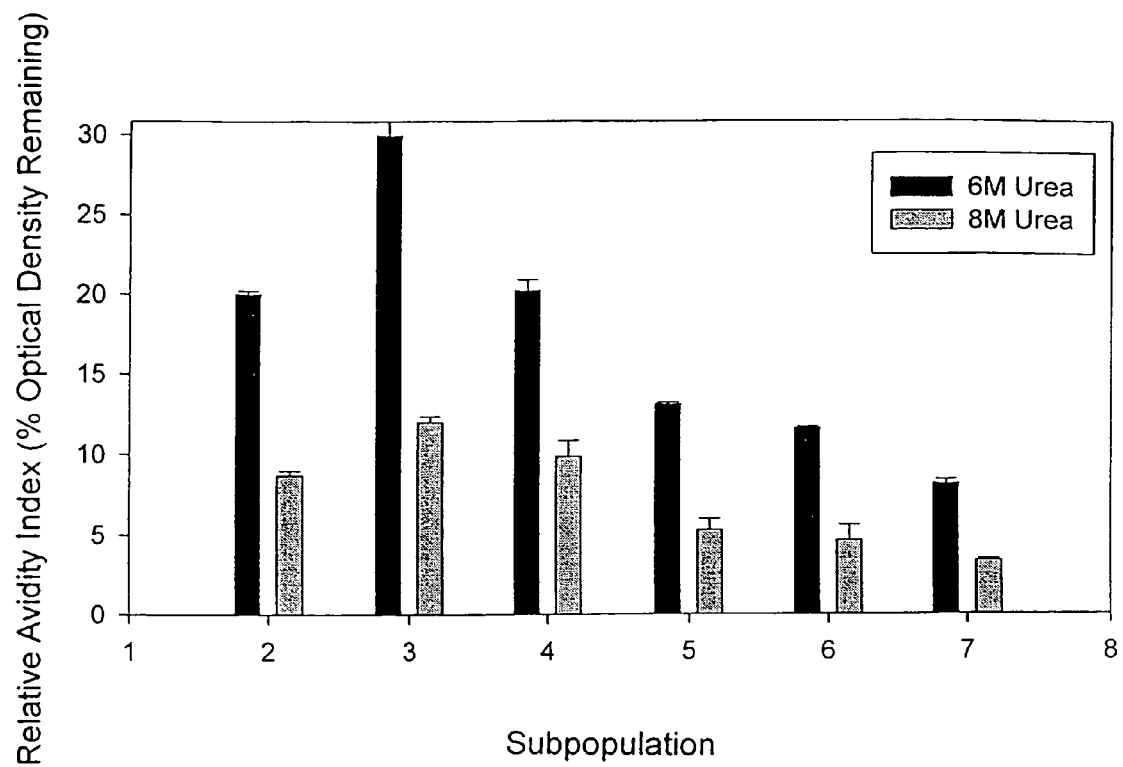
Figure 6A:
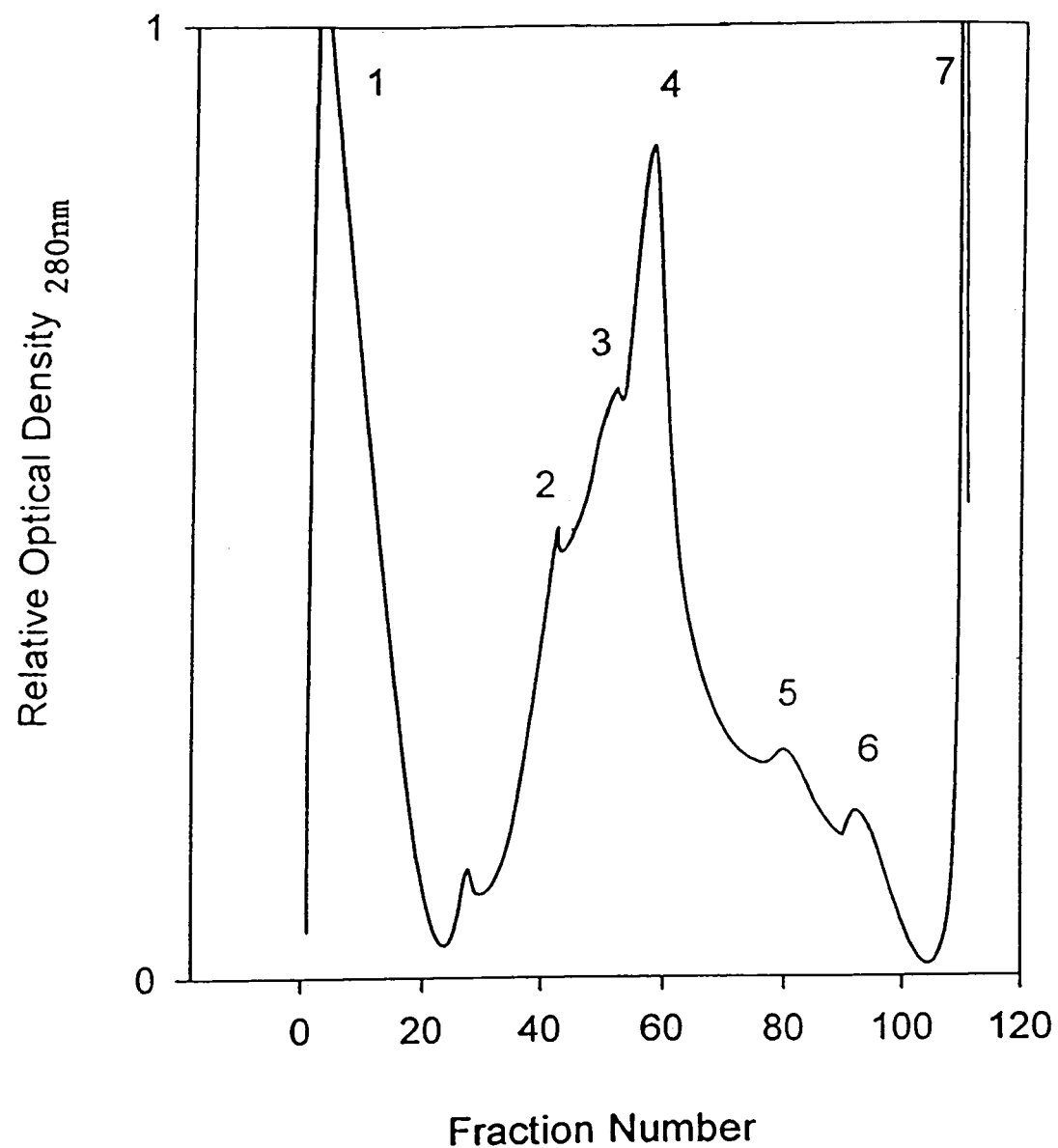
FIGS. 6A-6D are graphs showing: (6A) IDA-$Fe^{3+}$ chromatography of immune serum taken three weeks post-vaccination from hens receiving n-hexadecane emulsion containing polyoxyethylene sorbitan trioleate and sorbitan trioleate; (6B) ELISA end-point comparisons for serum from hens receiving n-hexadecane emulsion containing polyoxyethylene sorbitan trioleate and sorbitan trioleate or n-hexadecane emulsion containing polyoxyethylene sorbitan monooleate and sorbitan monooleate; (6C) comparison of the Relative Avidity Indexes (6M Urea) for serum from hens receiving n-hexadecane emulsion containing polyoxyethylene sorbitan trioleate and sorbitan trioleate and n-hexadecane emulsion containing polyoxyethylene sorbitan monooleate and sorbitan monooleate; (6D) comparison of the Relative Avidity Indexes (8M Urea) for serum from hens receiving n-hexadecane emulsion containing polyoxyethylene sorbitan trioleate and sorbitan trioleate and n-hexadecane emulsion containing polyoxyethylene sorbitan monooleate and sorbitan monooleate.
Figure 6B:
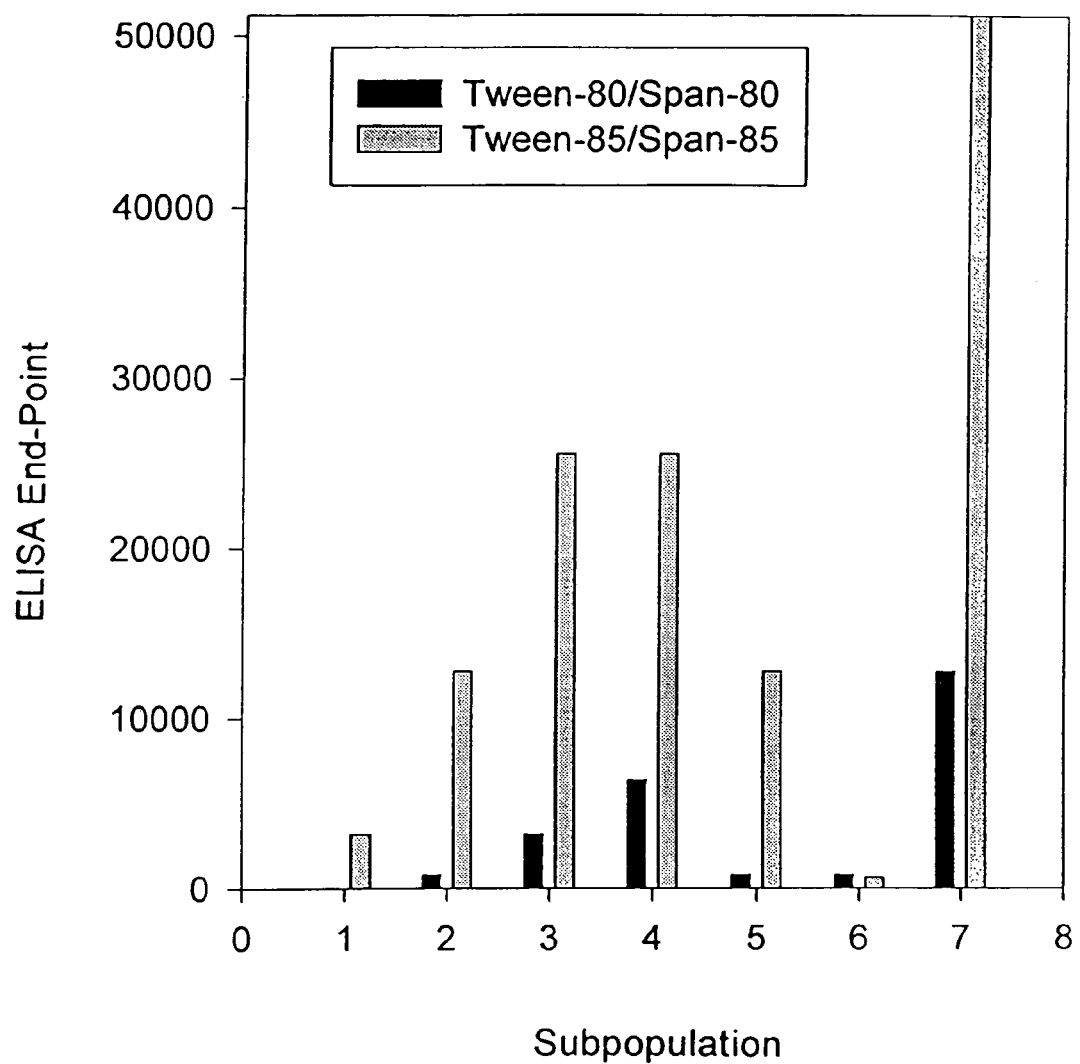
Figure 6C:
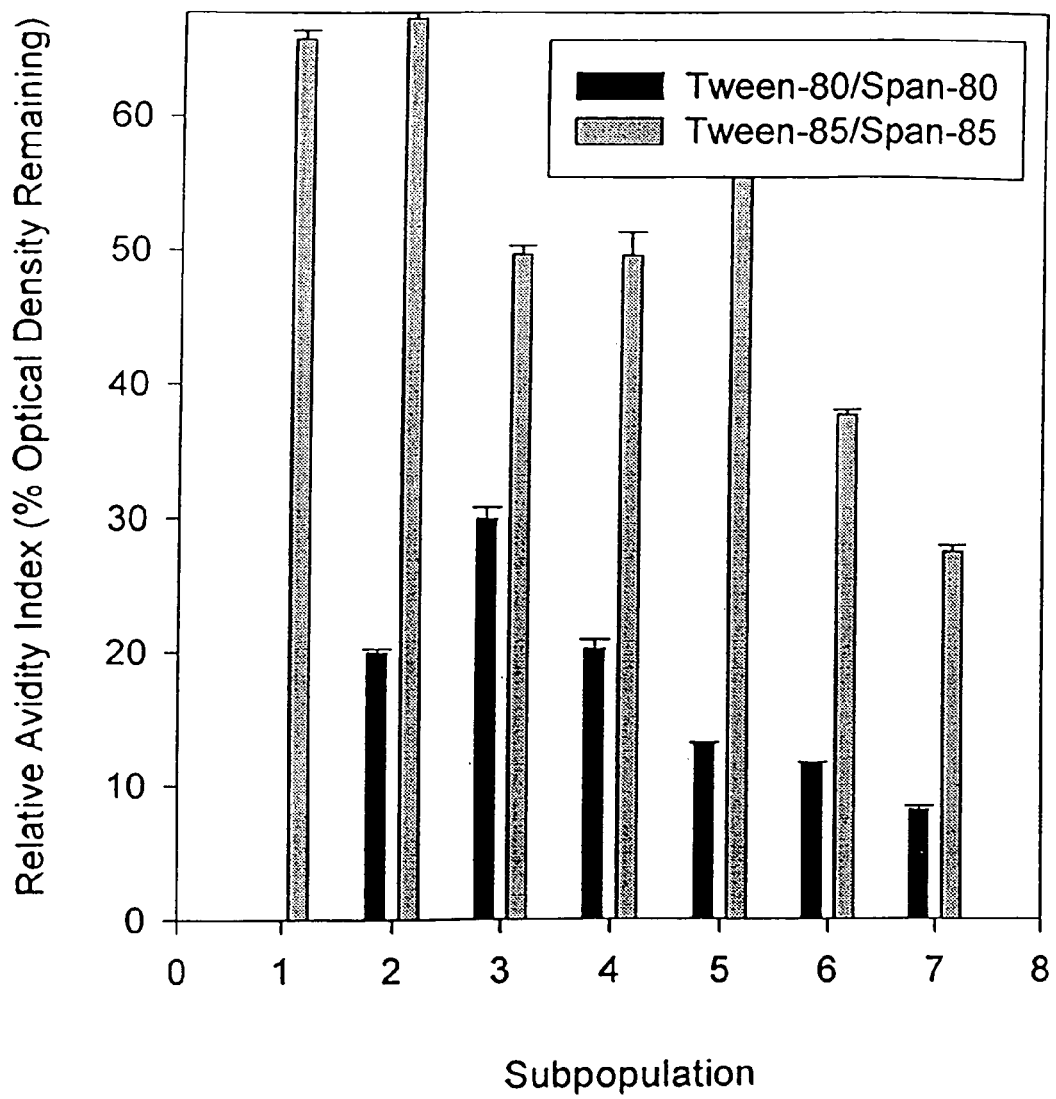
Figure 6D:
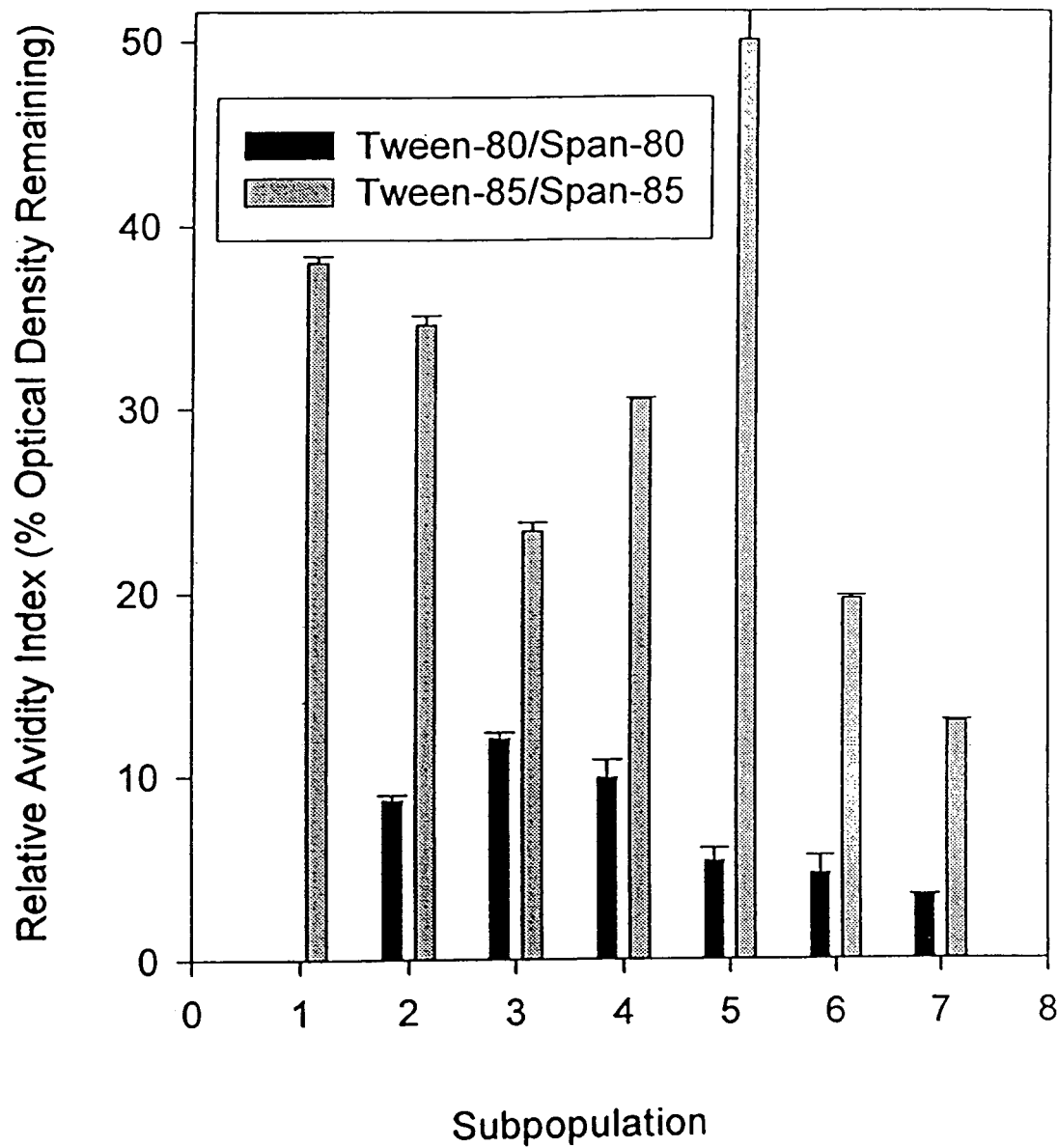
Figure 7A:
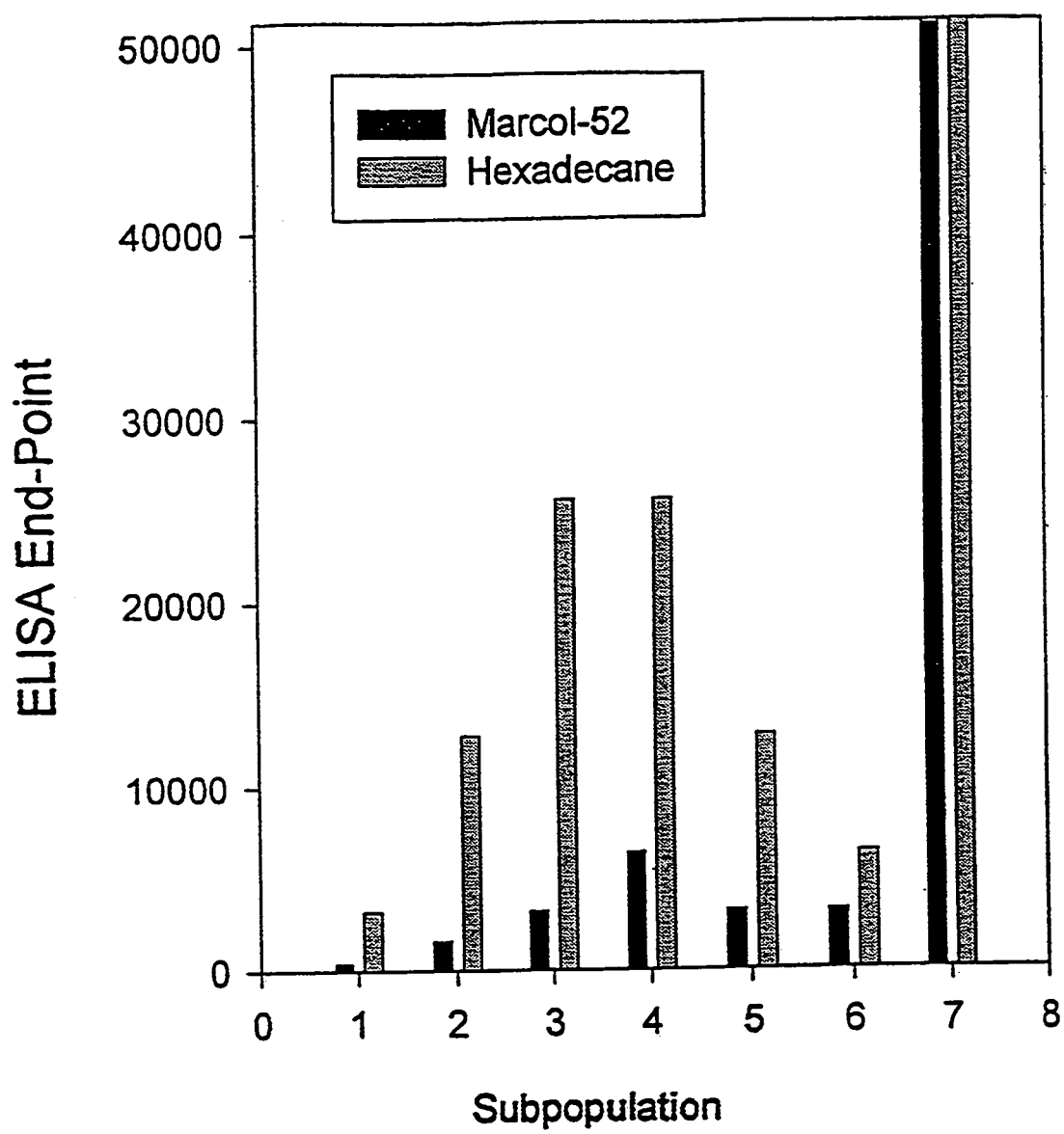
FIGS. 7A-7C are graphs showing: (7A) comparison of the ELISA end-points of immune serum taken three weeks post-vaccination from hens receiving MARCOL 52 and n-hexadecane emulsions containing polyoxyethylene sorbitan trioleate and sorbitan trioleate; (7B) comparison of the Relative Avidity Indexes (6M Urea) for serum from hens receiving MARCOL 52 and n-hexadecane emulsions containing polyethylene sorbitan trioleate and sorbitan trioleate; and (7C) comparison of the Relative Avidity Indexes (8M Urea) for serum from hens receiving MARCOL 52 and n-hexadecane emulsions containing polyoxyethylene sorbitan trioleate and sorbitan trioleate.
Figure 7B:
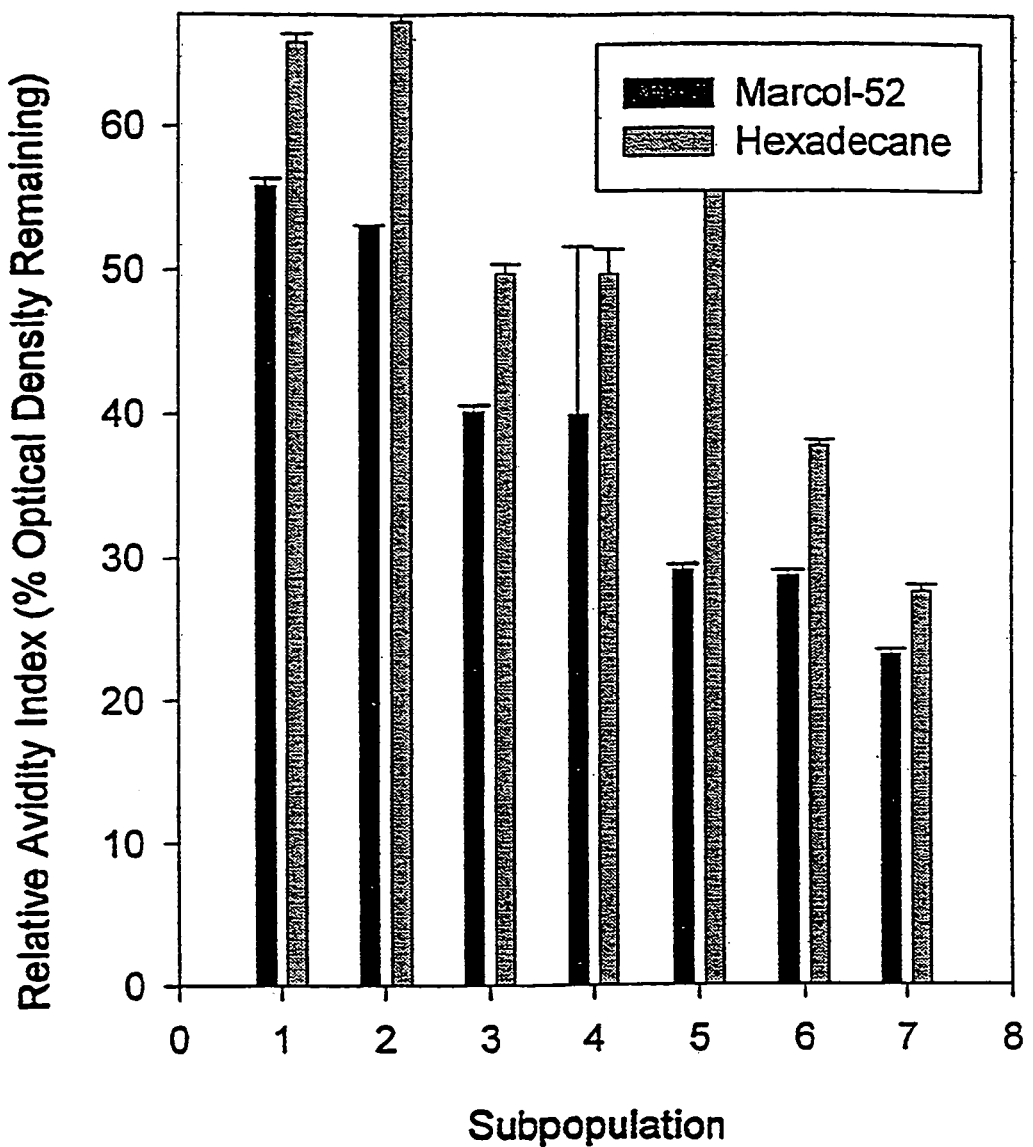
Figure 7C:
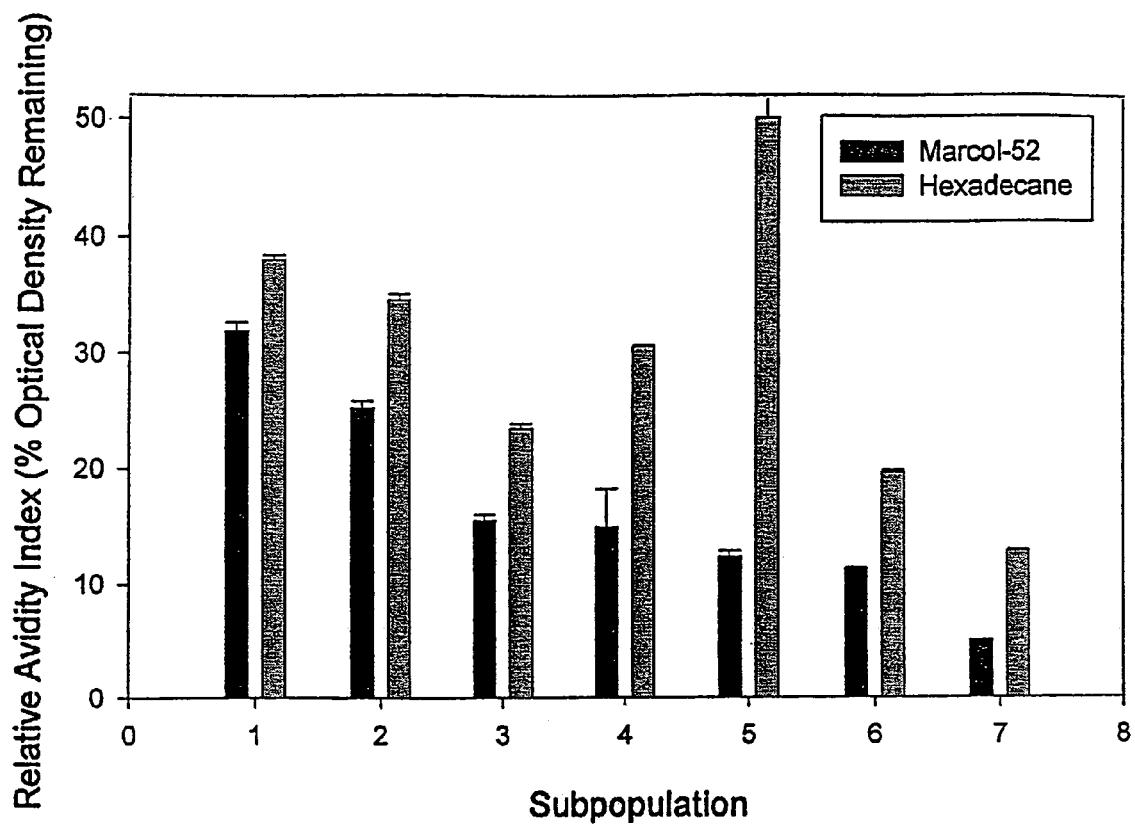

In the n-hexadecane emulsion vaccine containing polyoxyethylene sorbitan monooleate (TWEEN 80) and sorbitan monooleate (SPAN 80) (FIGS. 5A-5D), immunological activity was detected in peaks 2-7, while peak 1 demonstrated no activity (FIG. 58). The relative avidity index was comparable to that obtained for the mineral oil emulsion containing TWEEN 80 and SPAN 80 (FIG. 5C). When n-hexadecane was formulated with polyoxyethylene sorbitan trioleate (TWEEN 85) and sorbitan trioleate (SPAN 85) (FIGS. 6A-6D), both the immunological activity (FIG. 6B) and the relative avidity index for all subpopulations were significantly upregulated (FIGS. 6C and 6D). The relative avidity index and the immunological activity for the n-hexadecane emulsion containing TWEEN 85 and SPAN 85 was significantly higher statistically (P<0.001) over the n-hexadecane emulsion containing TWEEN 80 and SPAN 80, and the mineral oil emulsion containing TWEEN 85 and SPAN 85 (P=0.000122) (FIGS. 7A-7C).

Example 2

Hens were vaccinated and boosted about 4 weeks post primary vaccination with an inactivated *Salmonella enterica* serovar. *enteriditis* water-in-oil vaccine containing hexadecane and Arlacel 80, polyoxyethylene sorbitan trioleate and sorbitan trioleate (SEPRL vaccine) as described above in Example 1. Another group of hens was vaccinated and boosted about 4 weeks post primary vaccination with three commercially available *Salmonella enterica* serovar. *enteriditis* water-in-oil vaccines from Maine Biological Laboratories, Fort Dodge Animal Health, and Bioimmune. The vaccines were (1) Layermune SE (Bioimmune Co., Lenexa, Kans.) (BIO), (2) Poulvac SE (Fort Dodge Animal Health, Overland Park, Kans.) (FtD), and (3) Inactivac/SE4 (Maine Biological Laboratories, Waterville, Me.) (MBL). Non-immunized birds were used as the control. Three weeks following the boost, all hens were challenged with about $1 \times 10^8$ S. enteriditis. Tissues were taken and cultured on the days 13 and 19 post boost (FIGS. 7A-7D). Hens were sacrificed by cervical dislocation and a portion of the liver, the whole spleen, a portion of the ovaries, and a portion of the right cecum were aseptically removed and placed into pre-tared sterile stomacher bags. For each bird, the liver and spleen samples were combined while the ovaries and the cecum were placed in individual bags. The samples were diluted about 1:10 in tetrathionate brilliant green (Difco Laboratories, Detroit, Mich.) and stomached for about 60 seconds. The stomached samples (about 0.1 ml) were plated onto Brilliant Green agar containing about 20 µg/ml novobiocin (Sigma Chemical Co., St. Louis, Mo.) and about 20 µg/ml nalidixic acid (BGNN) (Sigma Chemical Co.). The cecum samples were serially diluted (about 10 fold) in phosphate-buffered saline, and about 0.1 ml samples were incubated overnight at about 37° C., and SE colony-forming units (CFU) was determined by plate count. For any negatives, about 0.1 ml of the respective tetrathionate enrichment was plated onto BGNN, which were then incubated overnight at about 37° C. As the enumeration method had a minimum detection threshold of about $1 \times 10^2$ CFU/g, samples that were negative for direct enumeration but positive after tetrathionate enrichment were arbitrarily assigned a value of about 50 CFU/g. The numbers of SE CFU/g in each treatment group were transformed to $\log_{10}$ then means were calculated. Statistical differences were determined by one-way analysis of variance using GraphPad Software (San Diego, Calif.) at P<0.05. Groups with different letters are significantly different on that particular day. Two trials were conducted.

Figure 8A:
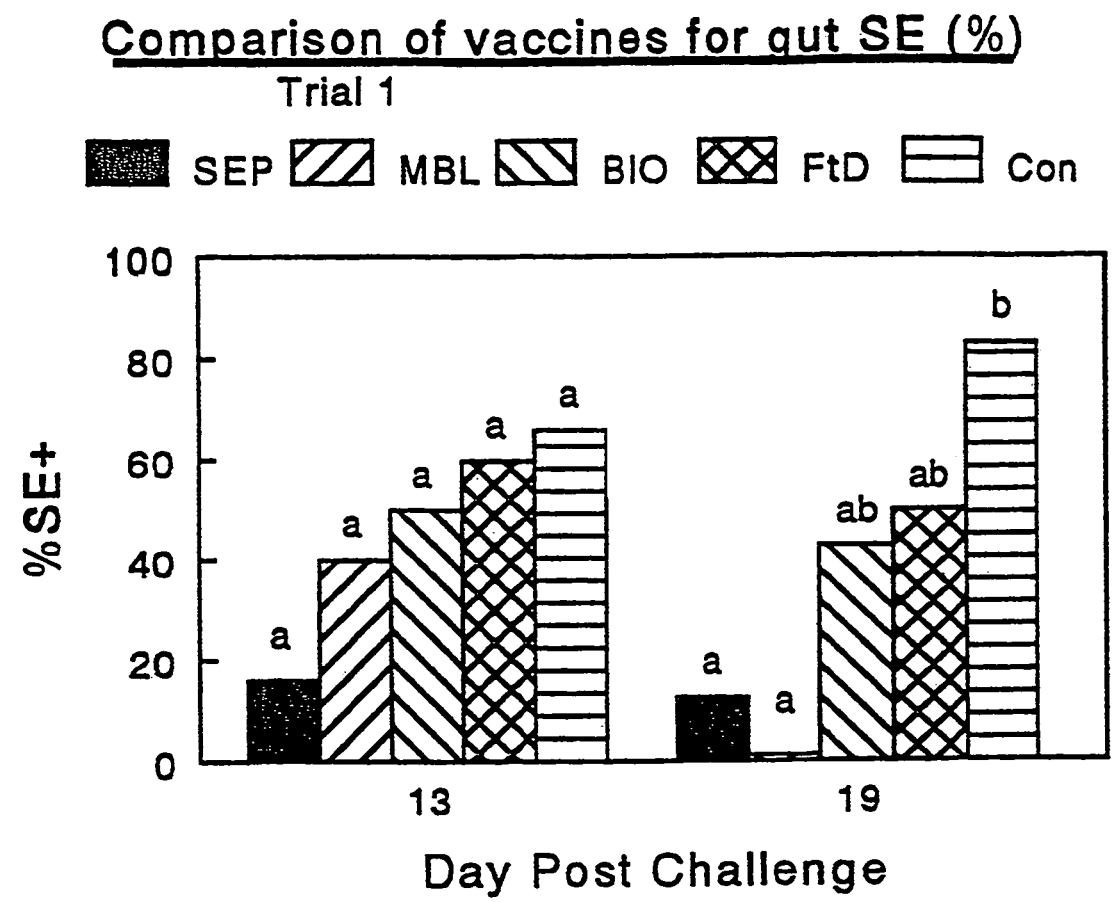
FIGS. 8A-8D are graphs showing comparison of protection against *Salmonella enteriditis* (SE) infection in hens receiving n-hexadecane inactivated SE emulsions containing polyoxyethylene sorbitan trioleate, sorbitan trioleate, and sorbitan monooleate versus three commercially available vaccines (1) Layermune SE (Bioimmune Co., Lenexa, Kans.) (BIO), (2) Poulvac SE (Fort Dodge Animal Health, Overland Park, Kans.) (FtD), and (3) Inactivac/SE4 (Maine Biological Laboratories, Waterville, Me.) (MBL); and control (non-immunized hens).
Figure 8B:
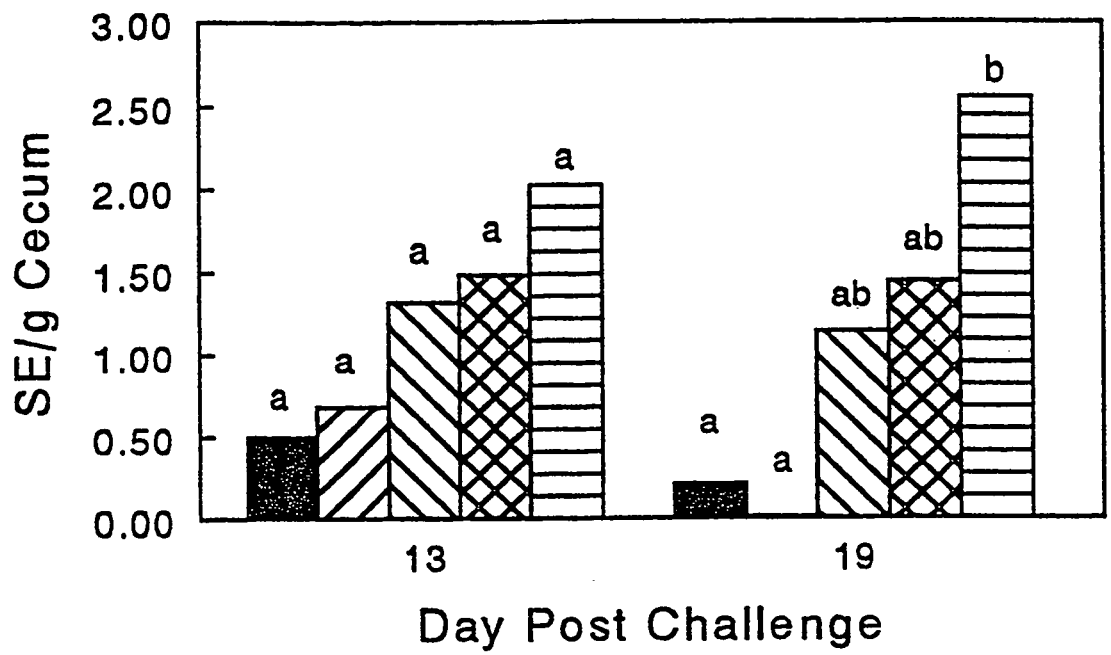
Figure 8C:
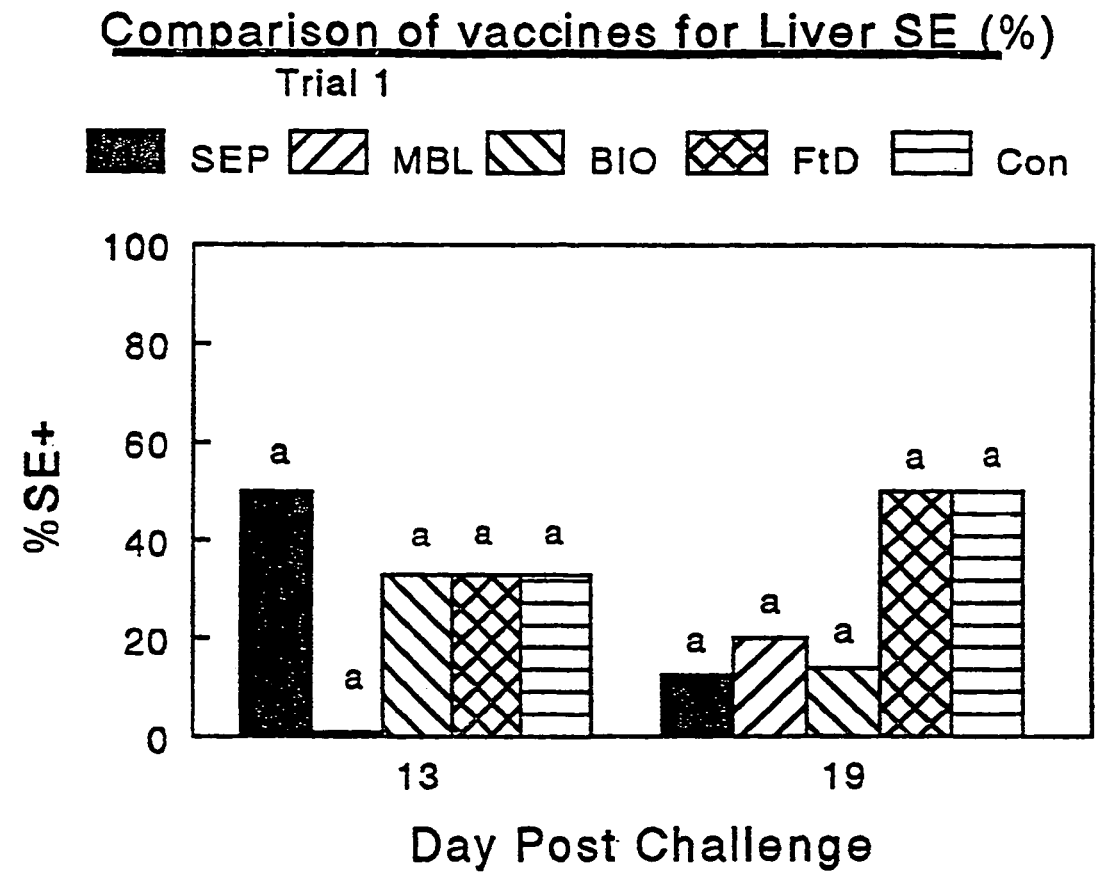
Figure 8D:
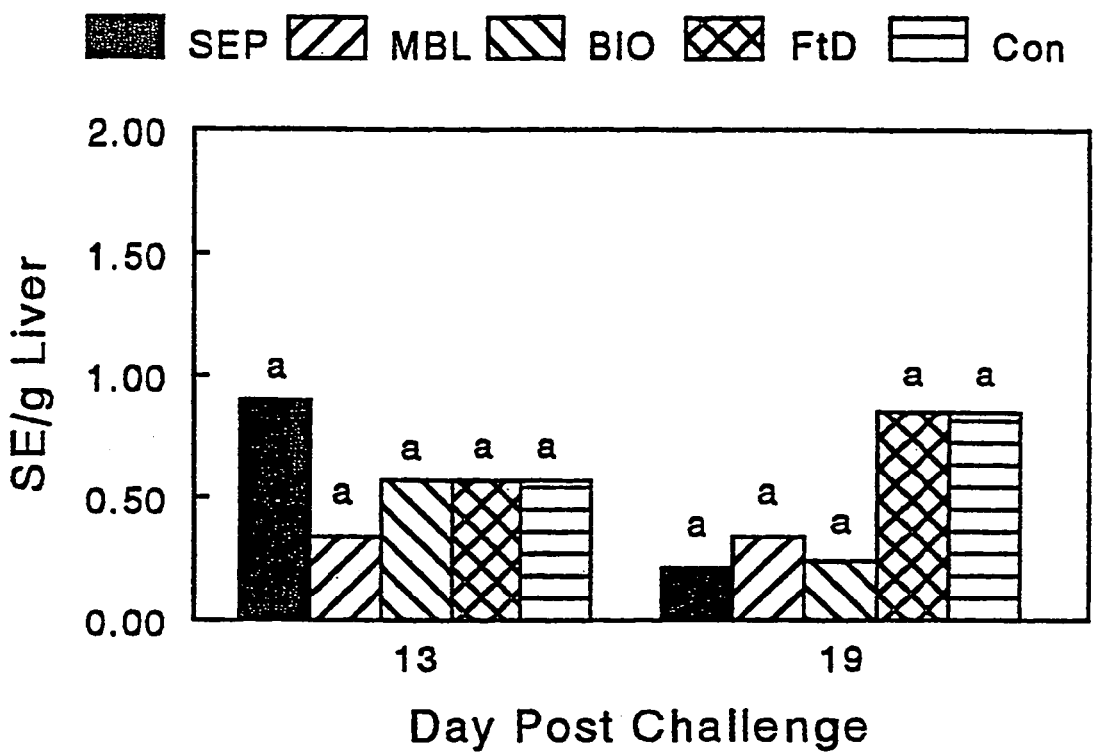

In Trial 1 (FIGS. 8A-8D), the % of intestinal SE+ hens was lower in the hens receiving the vaccine of the present invention (SEPRL) compared to the three commercial vaccines at day 13 post challenge and lower levels were observed at day 19 post challenge compared with hens receiving the commercial vaccines (FIGS. 8A and 8B). Internal extraintestinal organ levels were less affected by the SEPRL vaccine (FIGS. 8C and 8D).

Figure 9A:
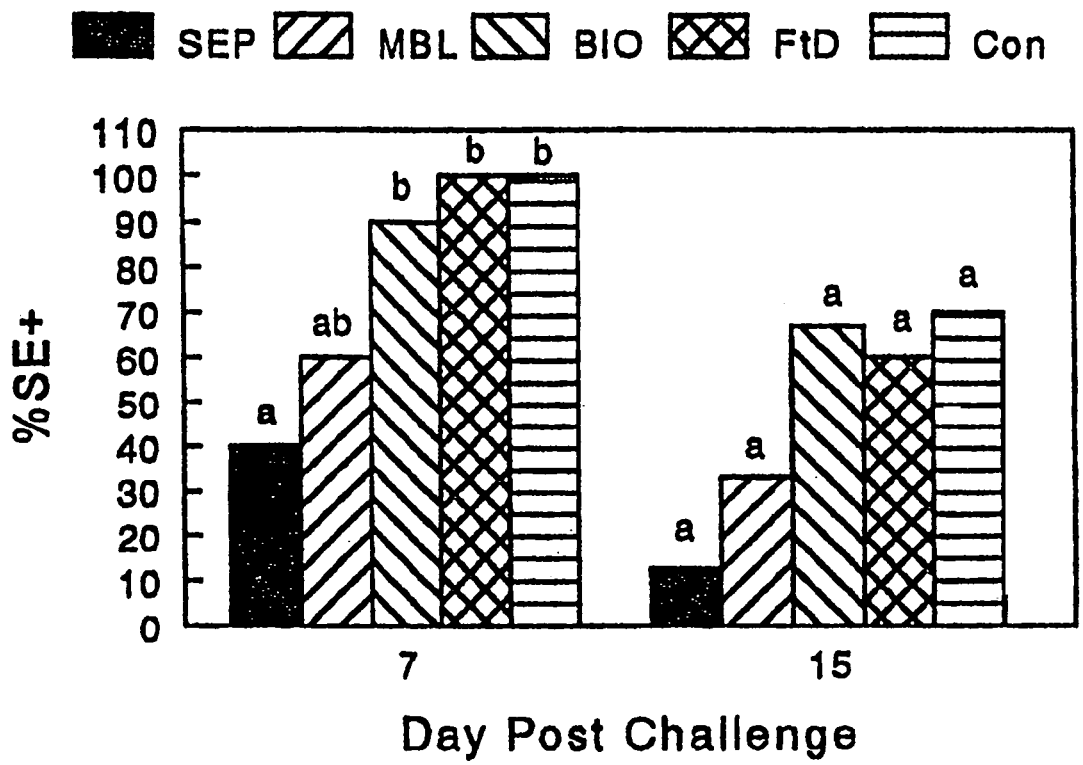
FIGS. 9A-9D are graphs showing comparisons of protection against SE infection in hens receiving n-hexadecane inactivated SE emulsions containing polyoxyethylene sorbitan trioleate, sorbitan trioleate, and sorbitan monooleate versus three commercially available vaccines (1) Layermune SE (Bioimmune Co., Lenexa, Kans.) (BIO), (2) Poulvac SE (Fort Dodge Animal Health, Overland Park, Kans.) (FtD), and (3) Inactivac/SE4 (Maine Biological Laboratories, Waterville, Me.) (MBL); and control (non-immunized hens).
Figure 9B:
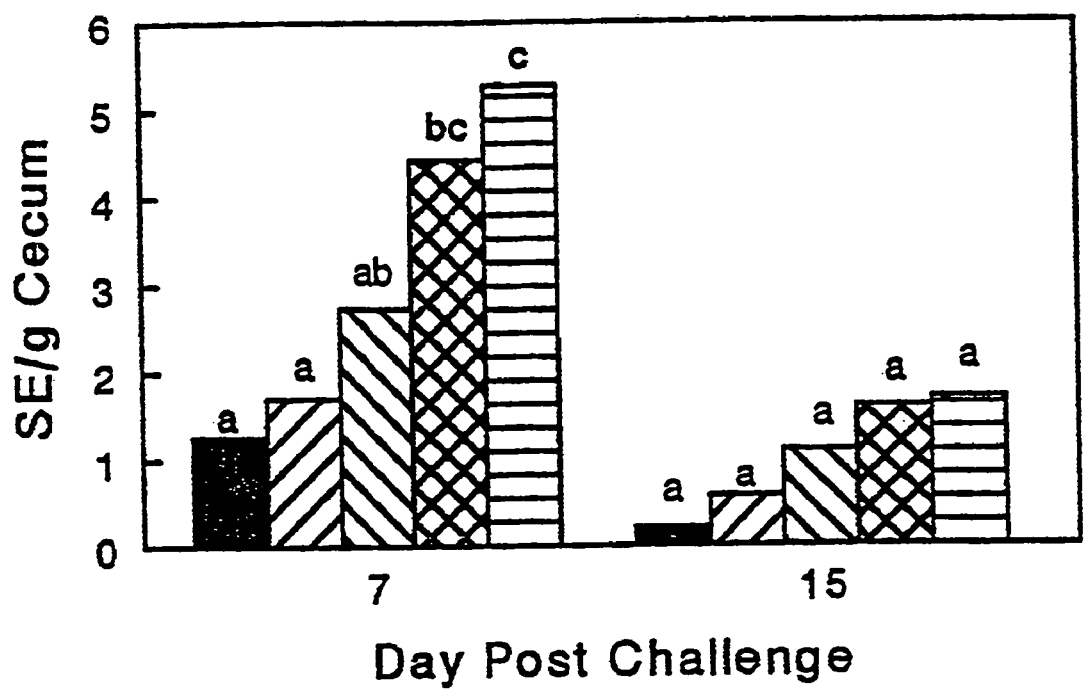
Figure 9C:
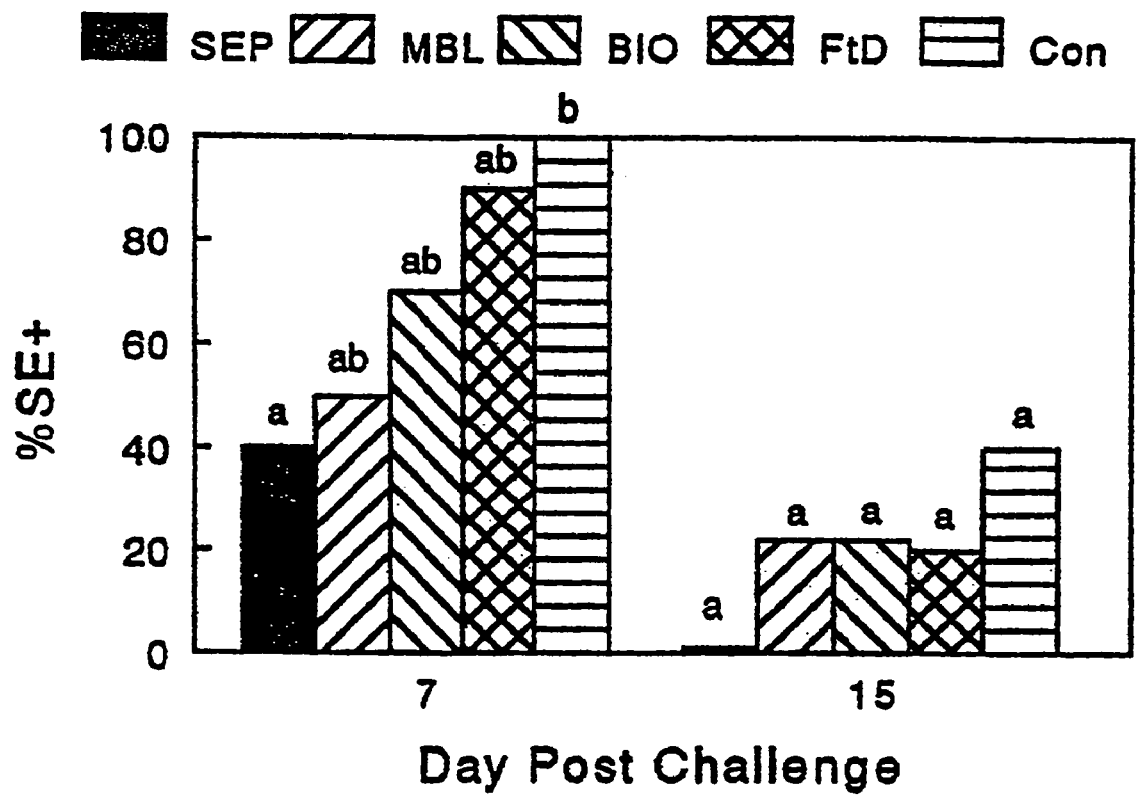
Figure 9D:
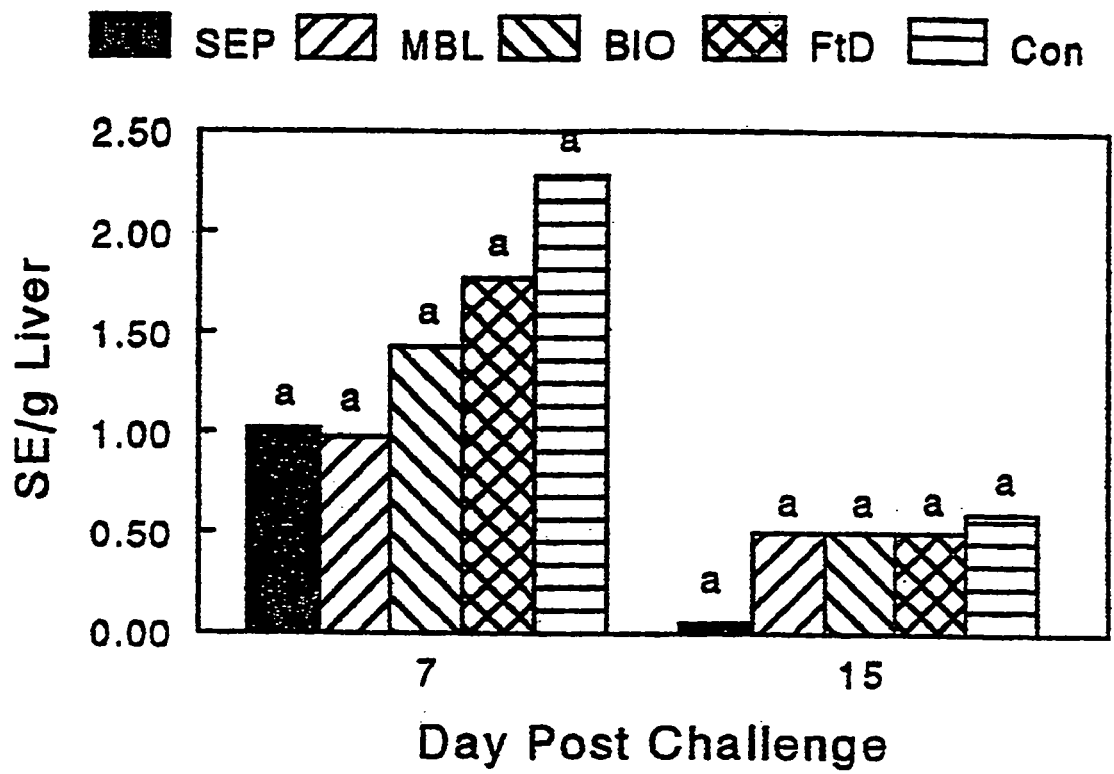

In trial 2 (FIGS. 9A-9D), significantly fewer hens receiving the SEPRL vaccine were intestinally SE+ compared with two of the commercial vaccines (FIGS. 9A and 9B). At day 15 post challenge, fewer hens were intestinally SE+, though not significantly, in the SEPRL vaccinated group compared to the commercial groups. Internal organ levels were numerically less in the SEPRL vaccinated group compared to the commercial groups (FIGS. 9C and 9D). Blood was drawn weekly from the vaccinated birds for serum. Bile was collected from sacrificed birds at the termination of the experiment on weeks 8 and 9. Microagglutination titers against SE stained antigen were determined on sera and bile according to methods previously described using serial two-fold dilutions of an original dilution of each sample (Gast et al., Avian Dis., Volume 37, 6, 992-999, 1992; herein incorporated by reference). See Table 1 for results. Serum and bile anti-SE titers were elevated in hens vaccinated with the vaccine of the present invention compared with the three commercial vaccines.

TABLE 1

Comparison of serum and biliary microagglutination (# of positive wells) for Hexadecane, MBL, Bioimmune, and Ft. Dodge

| | WEEK | | | | | | | |
| --- | --- | --- | --- | --- | --- | --- | --- | --- |
| Vaccine | Serum 2 | Serum 3 | Serum 4 | Serum 5 | Serum 6 | Serum 7 | Bile 8 | Bile 9 |
| Hexadecane | 11 | 9.91 | | 9.32 | 9.45 | 9.04 | 7.6 | 6.6 |
| MBL | 9.64 | 8.92 | | 8.44 | 8.66 | 8.33 | 5.8 | 5.11 |
| Bioimune | 9.79 | 8.68 | | 8.29 | 7.46 | 6.6 | 4.8 | 4.33 |
| Ft. Dodge | 8.16 | 7.92 | | 6.92 | 7.92 | 8.0 | 4.8 | 4.8 |

Example 3

Figure 10A:
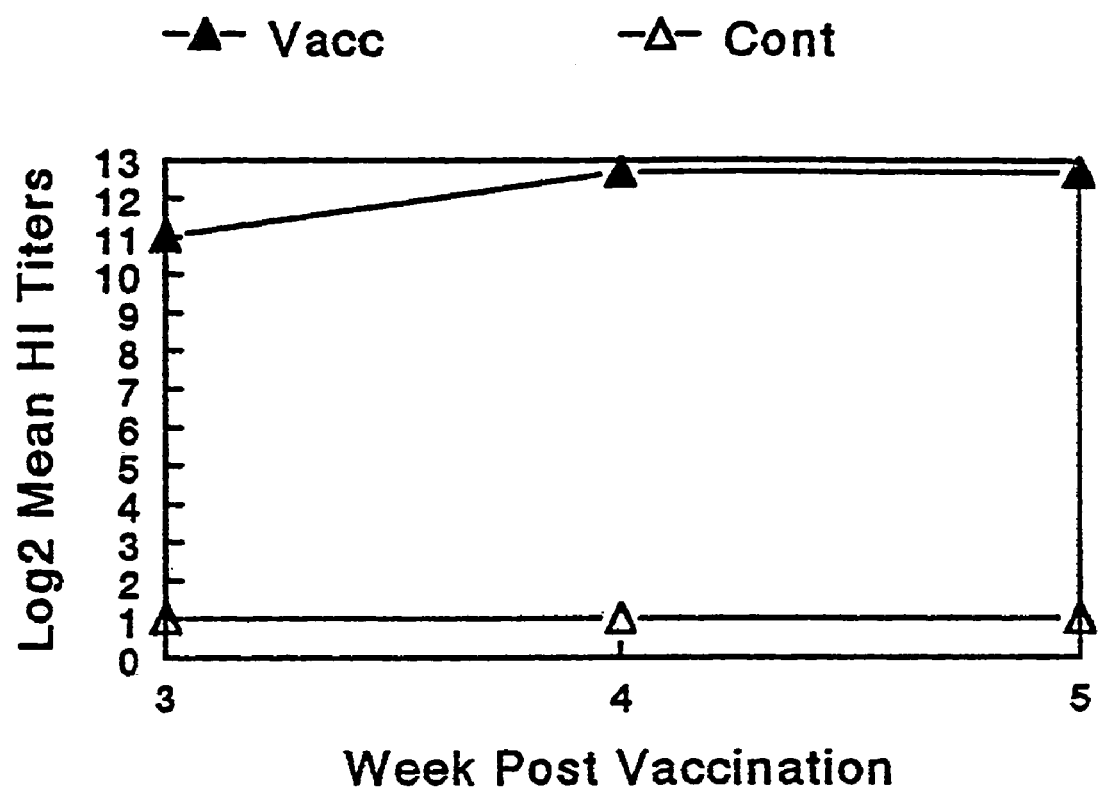
FIG. 10a is a graph showing serum HI-titers in hens receiving Avian Influenza Virus n-hexadecane vaccine.
Figure 10B:
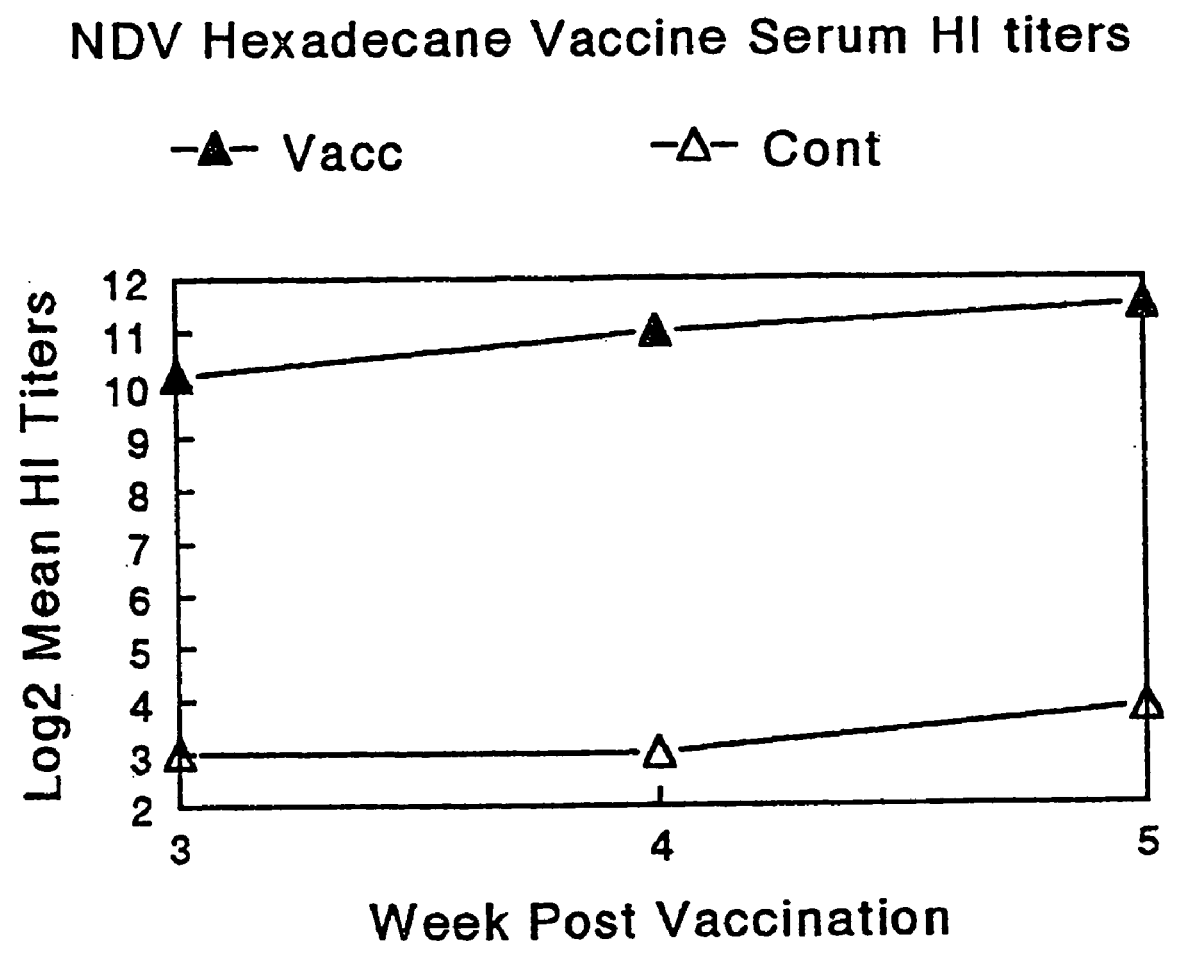

Water-in-oil vaccines for viruses were prepared using the same adjuvant base and procedures as for the Salmonella bacterin described above in Example 1. Vaccine antigen for Turkey Wis. 68 (M) and La Sota NDV was prepared from virus propagated in 9-day-old chicken embryos and harvested in the allantoic fluids (Beard et al., Avian Dis., Volume 19, 692-699, 1975; herein incorporated by reference). Inactivation of the fluids was with beta-propriolactone (BPL) as described by Beard et al. (supra). One milliliter of vaccine emulsion containing about 0.25 ml of AI allantoic antigen or about 1 mg of NDV antigen was given subcutaneously in the mid-dorsal neck region. Sera, in groups of six chickens, vaccinated at 4-weeks-old, were tested for hemagglutination-inhibition titers (Beard et al., supra) at 3, 4 and 5 weeks post vaccination. The antiviral titers were exceptionally high (FIGS. 10A and 10B). Chickens receiving n-hexadecane emulsions of the present invention containing avian influenza virus (AIV) and Newcastle Disease Virus (NDV) exhibited exceptionally elevated anti-viral titers (FIGS. 10A and (10B).

Example 4

A series of fatty acid esters were formulated to test their ability to enhance secondary immune responses in chickens. The fatty acid esters tested included butyl stearate, butyl myristate, tridecyl stearate, octastearate, isopropyl myristate, isocetyl myristate, isocetyl stearate, and isopropyl isostearate. These esters were formulated as water-in-oil emulsion vaccines using about 8 ml of fatty acid ester, about 1 ml IMWITOR 780K (isostearyl diglyceryl succinate; Sasol, South Africa), plus about 0.7 ml TWEEN-85 add about 0.3 ml SPAN 85 surfactants (Stone, H. D., Avian Dis., July-September, Volume 41(3), 591-597, 1997; herein incorporated by reference) and about 1 mg of antigen. Birds were vaccinated by the subcutaneous route in the mid-dorsal region of the neck. Each bird received about a 1 mg dose of acetone inactivated SE upon primary immunization and the secondary boost about 6 weeks later. The time frame between the primary immunization and the secondary boost was about 6 weeks (Davis and Glick, Poult. Sci., May, Volume 67(5), 855-857, 1988; herein incorporated by reference). At about three weeks post-secondary boodt, the immunological activity and the relative avidity index for each IgG subpopulation was determined (Tables 2a-2c). These results indicated that fatty acid ester priming emulsions initiate a stronger secondary immune response than to those vaccines which have mineral oil.

TABLE 2a

ELISA Activity for Secondary Immune Response

| Fatty Acid Ester | IgG Subpopulations | | | | | |
|---|---|---|---|---|---|---|
| | 2 | 3 | 4 | 5 | 6 | 7 |
| Butyl Stearate | 819200 | | 819200 | | 204800 | 406600 |
| Butyl Myristate | 204800 | | 409600 | | 102400 | 409600 |
| Tridecyl Stearate | 204800 | 204800 | 204800 | 102400 | 204800 | 819200 |
| Octastearate | 204800 | | 204800 | 102400 | 102400 | 204800 |
| Isopropyl Myristate | 102400 | 102400 | 204800 | | 51200 | 204800 |
| Isocetyl Myristate | 204800 | 204800 | 204800 | | 204800 | 204800 |
| Isocetyl Stearate | 204800 | | 409600 | | 102400 | 204800 |
| Isopropyl Isostearate | 204800 | 204800 | 204800 | 204800 | 204800 | 204800 |

*Note: Not all IgG subpopulations were well resolved/present

TABLE 2b

Relative Avidity for Secondary Immune Responses (6 M Urea)

| Fatty Acid Ester | IgG Subpopulations | | | | | |
|---|---|---|---|---|---|---|
| | 2 | 3 | 4 | 5 | 6 | 7 |
| Butyl Stearate | 84.17 | | 78.07 | | 72 | 66.91 |
| Butyl Myristate | 77.49 | | 75.72 | | 62.62 | 54.26 |
| Tridecyl Stearate | 79.82 | 72.13 | 65.27 | 68.95 | 69.47 | 65.08 |
| Octastearate | 70.16 | | 75.47 | 70.56 | 69.64 | 67.66 |
| Isopropyl Myristate | 76.4 | 71.06 | 60.71 | | 54.24 | 58.55 |
| Isocetyl Myristate | 79.77 | 77.24 | 67.83 | | 69.03 | 66.56 |
| Isocetyl Stearate | 76.22 | | 70.78 | | 65.6 | 62.58 |
| Isopropyl Isostearate | 80.95 | 78.78 | 82.86 | 82.18 | 78.99 | 78.86 |

*Note: Relative Avidity Indexes are expressed as % optical density after treatment with 6 M Urea TABLE 2c Relative Avidity Indexes for Secondary Immune Responses (8 M Urea)
IgG Subpopulations

| Fatty Acid Ester | 2 | 3 | 4 | 5 | 6 | 7 |
|---|---|---|---|---|---|---|
| Butyl Stearate | 66.79 | | 58.50 | | 54.40 | 52.66 |
| Butyl Myristate | 67.73 | | 59.85 | | 49.09 | 39.3 |
| Tridecyl Stearate | 65.67 | 56.51 | 49.63 | 54.51 | 51.09 | 46.32 |
| Octastearate | 62.78 | | 58.01 | 56.26 | 54.75 | 41.82 |
| Isopropyl Myristate | 60.06 | 51.65 | 42.50 | | 35.89 | 38.14 |
| Isocetyl Myristate | 71.38 | 63.44 | 55.37 | | 53.88 | 49.57 |
| Isocetyl Stearate | 61.3 | | 51.12 | | 49.37 | 43.57 |
| Isopropyl Stearate | 68.78 | 67.25 | 65.25 | 64.94 | 61.92 | 59.21 |

*Note: Relative Avidity Indexes are expressed in % optical density remaining after treatment with 8 M Urea.

Example 5

A series of fatty acid esters were formulated into vaccine preparations to prime 18 day old white Plymouth Rock embryos to respond more fully to an SE hexadecane vaccine administered at about 3 weeks post hatch. The fatty acid esters tested included butyl stearate, butyl myristate, ethyl oleate, isopropyl isostearate, octyl palmitate, isopropyl palmitate, isopropyl oleate, and ethyl oleate. These esters were formulated as water-in-oil emulsions using IMWITOR 780K (isostearyl diglyceryl succinate; Sasol, South Africa.) plus TWEEN-85 and SPAN-85 surfactants. Embryos were immunized as described previously (Stone et al., Avian Dis., Volume 41, 856-863, 1997; herein incorporated by reference) using about 20 μg acetone inactivated SE in about 200 μl of respective emulsion. About three weeks post hatch, the birds were vaccinated by the subcutaneous route in the mid-dorsal region of the neck using about 1 ml of hexadecane vaccine containing about 1 mg acetone inactivated SE as described above in Example 1. All birds were bled weekly for the next 3 weeks post vaccination and microagglutination titers determined on serum from each group using methods previously described. Results are presented in Table 3 below and indicate that individuals receiving the in ovo vaccine containing the butyl stearate emulsion were primed to respond to secondary vaccination after hatch, exhibiting a decreased delay in responding to vaccination.

TABLE 3

Serum microagglutination titers for in ovo immunizations utilizing fatty acid ester priming emulsions.

| Fatty Acid Ester | WEEKS POST HATCH | | | |
|---|---|---|---|---|
| | 3 | 4 | 5 | 6 |
| Ethyl Oleate | | | 7.3 | 8.6 |
| Isopropyl Isostearate | | 6 | 7.5 | 9.7 |
| Butyl Stearate | 4.17 | 4.1 | 9.6 | 9.9 |
| Octyl Palmitate | | | 7.6 | 9.4 |
| Isopropyl Palmitate | | | 11.2 | 9.9 |
| Isopropyl Oleate | | | 9.3 | 10.5 |
| Isopropy Myristate | | | 9.6 | 10.9 |
| Butyl Myristate | | | 9.3 | 10 |
| Control | | | 9.3 | 9.8 |

For isopropyl isostearate, 4 out of 10 birds responded at 4 weeks post hatch or 1 week post revaccination.
For butyl stearate, 6 out of 10 birds responded at 3 weeks post hatch while 10 of 10 birds responded at 4 weeks or 1 week post-vaccination post hatch.

Example 6

A series of fatty acid esters were formulated into vaccine preparations to prime white Plymouth Rock chicks, 12 weeks of age, to respond more fully to an SE hexadecane vaccine administered at about 6 weeks following the priming vaccine. The fatty acid esters tested included butyl stearate, octastearate, isopropyl isostearate, isocetyl stearate, butyl myristate, isopropyl myristate, isocetyl myristate, and hexadecane (non-ester control). These esters were formulated as described above in Example 4 without including the SE antigen. Chicks were immunized as described previously (Stone et al., Avian Dis., 1997, supra) using about 1 ml of the respective priming emulsion vaccine. About six weeks after the priming emulsion vaccine, the birds were vaccinated by the subcutaneous route in the mid-dorsal region of the neck using about 1 ml of an n-hexadecane vaccine containing about 1 mg of acetone inactivated SE as described above in Example 1. All birds were bled weekly for the next three weeks post vaccination.

The immunological activity is shown in Table 4, relative avidity indexes for secondary immune response using 6M Urea are shown in Table 5 and using 8M urea shown in Table 6. The results indicate that butyl stearate (no antigen) is unique for stimulating high activity and avidity over about 2-7 subpopulations.

TABLE 4

ELISA activity for secondary immune response from birds initially immunized with experimental no-antigen containing fatty acid ester priming emulsions.

| Fatty Acid Ester | IgG subpopulations | | | | | |
|---|---|---|---|---|---|---|
| | 2 | 3 | 4 | 5 | 6 | 7 |
| Butyl Stearate | 102400 | 204800 | 204800 | 102400 | 102400 | 204800 |
| Octastearate | 51200 | 51200 | 102400 | 25600 | 25600 | 102400 |
| Isopropyl Isostearate | 25600 | 51200 | 25600 | | 12800 | 51200 |
| Isocetyl Stearate | 51200 | 25600 | 25600 | 25600 | 25600 | 51200 |
| Butyl Myristate | 102400 | 51200 | 204800 | | | |
| Isopropyl Myristate | 25600 | | 102400 | | 51200 | 102400 |
| Isocetyl Myristate | 3200 | 12800 | 51200 | | 6400 | 25600 |
| Hexadecane | 25600 | | 51200 | 6400 | 6400 | 51200 |

TABLE 5

Relative avidity indexes for secondary immune response from birds initially immunized with no-antigen fatty acid ester priming emulsions (6 M Urea).

| Fatty Acid Ester | IgG Subpopulations | | | | | | |
|---|---|---|---|---|---|---|---|
| | 2 | 3 | 4 | 5 | 6 | 7 | Ave. |
| Butyl Stearate | 82.77 | 69.15 | 70.29 | 66.44 | 64.24 | 59.85 | 68.79 |
| Octastearate | 67.32 | 60.93 | 50.56 | 50.33 | 51.49 | 48.31 | 54.82 |
| Isopropyl Isostearate | 43.96 | 39.73 | 37.24 | | 35.89 | 20.07 | 35.38 |
| Butyl Myristate | 69.73 | 53 | 51.42 | | | | 58.05 |
| Isopropyl Myristate | 39.34 | | 40.79 | 38.52 | 26.12 | 36.19 | |
| Isocetyl Myristate | 26.96 | 21.53 | 31.85 | 38.54 | | | 29.72 |
| Hexadecane | 28.4 | | 38.11 | 33.11 | 31.76 | 26.9 | 31.66 |

TABLE 6

Relative avidity indexes for secondary immune response from birds initially immunized with no-antigen fatty acid ester priming emulsions (8 M Urea)

| Fatty Acid Ester | IgG Subpopulations | | | | | | |
|---|---|---|---|---|---|---|---|
| | 2 | 3 | 4 | 5 | 6 | 7 | Ave. |
| Butyl Stearate | 70.45 | 57.07 | 50.71 | 49.12 | 48.97 | 41.08 | 52.9 |
| Octastearate | 51.95 | 39.5 | 27.15 | 24.68 | 24.26 | 23.77 | 31.88 |
| Isopropyl Isostearate | 18.01 | 20.21 | 17.93 | 16.43 | 10.15 | 16.55 | |
| Butyl Myristate | 39.07 | 29.67 | 32.33 | | | | 33.69 |
| Isopropyl Myristate | 24.96 | | 24.38 | | 23.11 | 12.65 | 21.27 |
| Isocetyl Myristate | 11.67 | 5.13 | 15.42 | | | 24.43 | 14.16 |
| Hexadecane | 9.09 | | 14.81 | 12.51 | 10.75 | 6.89 | 10.81 |

Example 7

Figure 11:
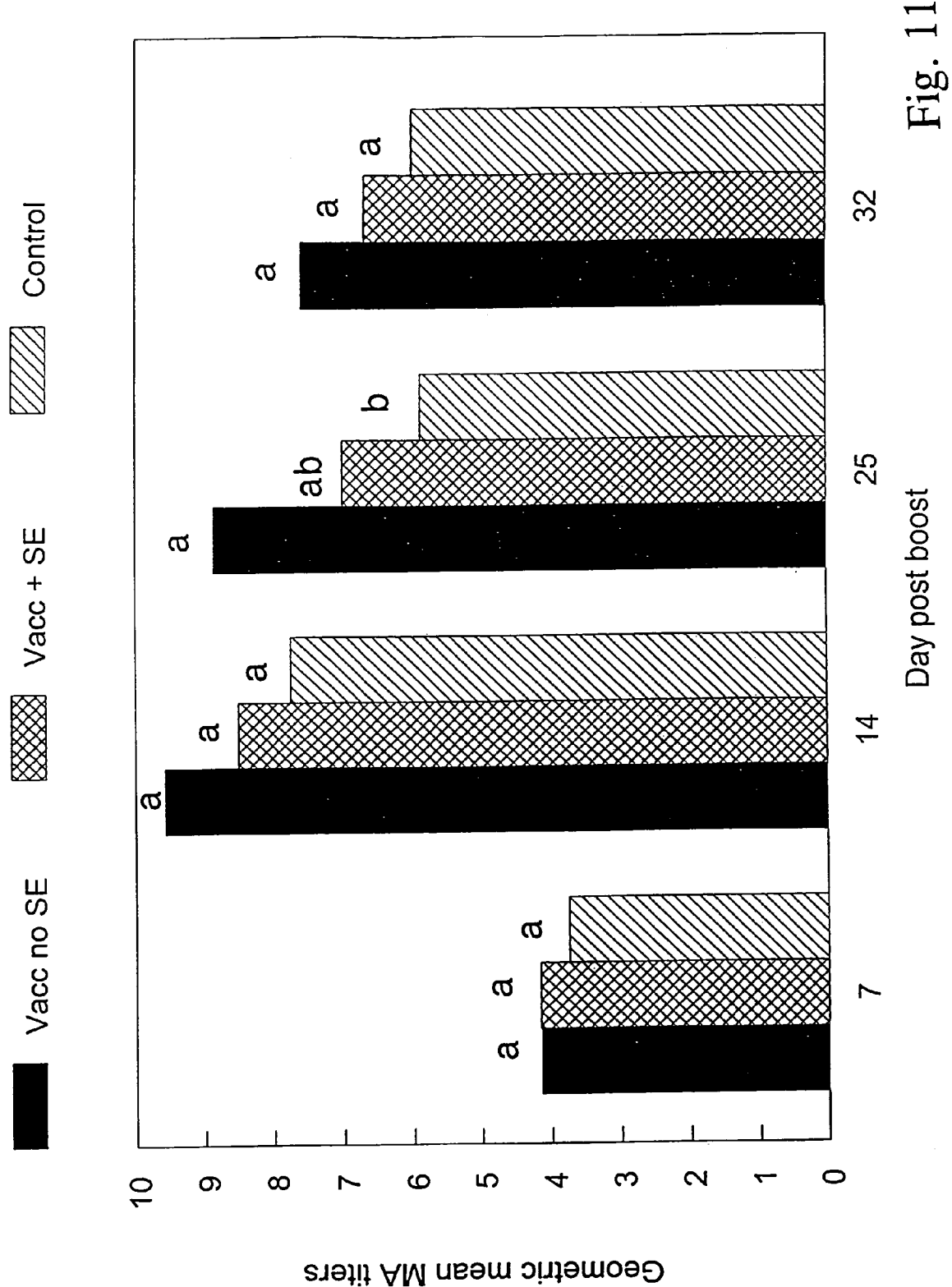
FIG. 11 is a graph showing anti-SE titers from in ovo priming emulsion vaccinated chicks then boosted with Fort Dodge Animal Health SE bacterin 14 days post hatch.

Eighteen day embryos received about 0.2 ml of a butyl stearate priming emulsion vaccine alone or with about 5 μg of killed SE antigen as described above in Example 5. A needle was inserted into the egg and withdrawn for the control. At fourteen days post hatch, all birds received about 0.3 ml of the Fort Dodge Animal Heath SE bacterin vaccine subcutaneously. As can be seen in FIG. 11, butyl stearate without antigen in the priming emulsion vaccine administered in ovo, causes a boost in response over control after receiving the commercial bacterin after hatch at day 25. Embryos receiving the priming emulsion vaccine with SE antigen also showed higher levels over control after day 25 but not as great as the priming vaccine without antigen.

Example 8

Figure 12A:
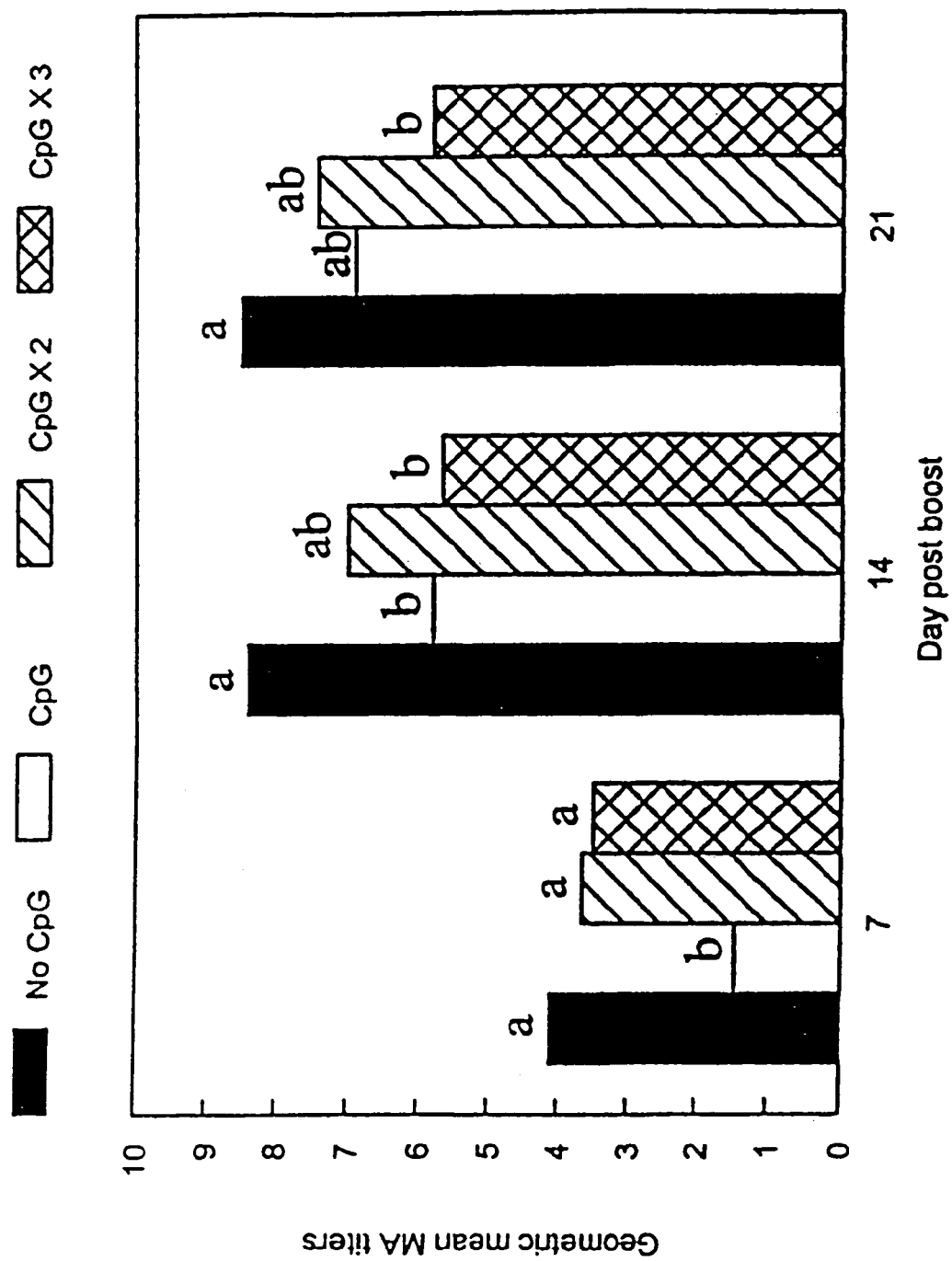
FIG. 12a is a graph showing anti-SE titers from in ovo priming emulsion vaccine with and without CpG, no antigen followed by a post hatch boost with Fort Dodge Animal Health vaccine or CpG and Fort Dodge Animal Health vaccine.
Figure 12B:
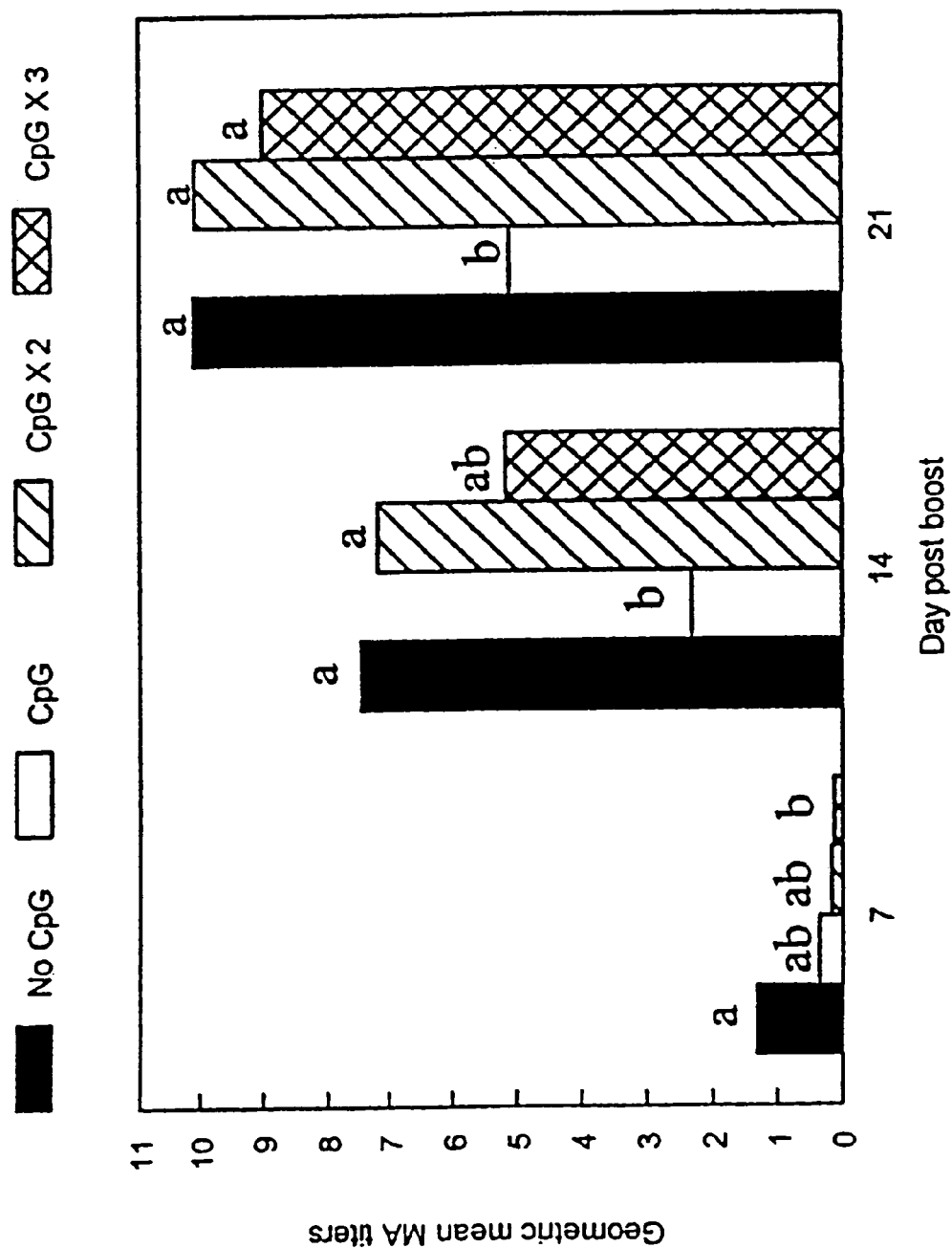
FIG. 12b is a graph showing anti-SE titers from in ovo priming emulsion vaccine with or without CpG, no antigen followed by a post hatch boost with Southeast Poultry Research Laboratory vaccine or CpG and Southeast Poultry Research Laboratory vaccine.

Eighteen day old embryos received about 0.2 ml of butyl stearate priming emulsion, as described above in Example 5, alone or with about 3 μg CpG motif. About 3 weeks post hatch, the group receiving butyl stearate with no CpG, was boosted with Fort Dodge Animal Heath SE bacterin or with a water-in-oil hexadecane SE emulsion (No CpG). CpG motifs are fragments of bacterial DNA which have been shown to enhance immunity in mammals and birds against a variety of pathogens. One group of birds that received the butyl stearate plus CpG was boosted subcutaneously at one week post hatch with about 0.3 ml Fort Dodge Animal Health SE bacterin or with about 0.3 ml water-in-oil hexadecane SE emulsion (CpG). A second group of birds that received butyl stearate plus CpG was boosted at one week post hatch with butyl stearate plus CpG followed by immunization with about 0.3 ml Fort Dodge Animal Heath SE bacterin or with about 0.3 ml water-in-oil hexadecane SE emulsion at two weeks post hatch (CpG×2). A third group of birds that received the butyl stearate plus CpG was boosted at about one and about two weeks post hatch with butyl stearate plus CpG followed by immunization with about 0.3 ml Fort Dodge Animal Health SE bacterin or with about 0.3 ml water-in-oil hexadecane SE emulsion at three weeks post hatch. FIGS. 12A and 12B, show that administering embryos with the butyl stearate emulsion alone can enhance the response to commercial or experimental antigen-containing vaccines. Administration of CpG motifs did not improve the response of the birds to the commercial SE bacterins.

The foregoing detailed description is for the purpose of illustration. Such detail is solely for that purpose and those skilled in the art can make variations without departing from the spirit and scope of the invention.

What is claimed:
1. An injectable water-in-oil emulsion composition for priming an animal for an enhanced secondary immune response consisting essentially of:
   (a) a $C_{18}$-$C_{32}$ fatty acid ester,
   (b) an emulsifier, and
   (c) a mixture of two nonionic surfactants;
wherein the injectable water-in-oil emulsion composition is without an antigen and primes an animal for an enhanced secondary immune response.

2. The emulsion of claim 1 wherein the $C_{18}$-$C_{32}$ fatty acid ester is selected from the group consisting of butyl stearate, butyl myristate, tridecyl stearate, octastearate, isostearate, and mixtures thereof.

3. The emulsion of claim 1 wherein said emulsifier is isostearyl diglycerol succinate.

4. The emulsion of claim 1 wherein said mixture of at least two nonionic surfactants includes polyoxyethylene sorbitan trioleate and sorbitan trioleate.

5. An injectable water-in-oil emulsion composition for priming an animal for an enhanced secondary immune response consisting essentially of:

(a) a $C_{18}$-$C_{32}$ fatty acid ester, (b) isostearyl diglycerol succinate, and (c) a mixture of polyoxyethylene sorbitan trioleate and sorbitan trioleate; wherein the injectable water-in-oil emulsion composition is without an antigen and primes an animal for an enhanced secondary immune response.

\* \* \* \* \*